(12) United States Patent
Nunley et al.

(10) Patent No.: US 9,220,491 B2
(45) Date of Patent: Dec. 29, 2015

(54) LATERAL ACCESS SYSTEM AND METHOD OF USE

(71) Applicant: K2M, Inc., Leesburg, VA (US)

(72) Inventors: Pierce Nunley, Shreveport, LA (US); Colin Natali, London (GB); Faheem Sandhu, Washington, DC (US); Ronald Childs, Fairfax, VA (US); Brandon Moore, Summit Point, WV (US)

(73) Assignee: K2M, INC., Leesburg, VA (US)

( * ) Notice: Subject to any disclaimer, the term of this patent is extended or adjusted under 35 U.S.C. 154(b) by 328 days.

(21) Appl. No.: 13/871,657

(22) Filed: Apr. 26, 2013

(65) Prior Publication Data

US 2013/0237767 A1 Sep. 12, 2013

Related U.S. Application Data

(63) Continuation of application No. 13/270,588, filed on Oct. 11, 2011, now Pat. No. 8,449,463.

(60) Provisional application No. 61/391,402, filed on Oct. 8, 2010.

(51) Int. Cl.
*A61B 1/32* (2006.01)
*A61B 17/02* (2006.01)
(Continued)

(52) U.S. Cl.
CPC .............. *A61B 17/025* (2013.01); *A61B 1/32* (2013.01); *A61B 17/0206* (2013.01); *A61B 17/885* (2013.01); *A61F 2/4465* (2013.01); *A61F 2/4611* (2013.01); *A61B 17/1671* (2013.01); *A61B 17/1757* (2013.01); *A61B 17/3468* (2013.01); *A61B 17/8897* (2013.01); *A61B 2017/0256* (2013.01); *A61B 2019/462* (2013.01); *A61F 2/4684* (2013.01); *A61F 2002/2835* (2013.01); *A61F 2002/3023* (2013.01);
(Continued)

(58) Field of Classification Search
CPC ................ A61B 1/32; A61B 17/0206; A61B 2017/0256
See application file for complete search history.

(56) References Cited

U.S. PATENT DOCUMENTS

| 3,749,088 A | 7/1973 | Kohlmann |
|---|---|---|
| 5,813,978 A | 9/1998 | Jako |

(Continued)

OTHER PUBLICATIONS

International Search Report from International Application No. PCT/US2011/055742 mailed on Feb. 3, 2012.
(Continued)

*Primary Examiner* — Christian Sevilla
(74) *Attorney, Agent, or Firm* — Carter, DeLuca, Farrell & Schmidt, LLP

(57) ABSTRACT

A surgical access device including a frame, first and second supports, and first and second retractor blades releasably coupled with the first and second supports, respectively. The frame has first and second arms. The first support is releasably coupled with the first and second arms. The second support is slidably mounted on the first and second arms. The second support is movable between a first position with the retractor blades in close cooperative position and a spaced apart position with respect to the first support. The first and second retractor blades each have a distal end portion configured and adapted to engage a vertebral body. In one method of use, the retractor is inserted through an incision in first orientation with the blades in close approximation and rotated approximately 90°, before spreading the retractor blades to retract tissue.

56 Claims, 27 Drawing Sheets

(51) Int. Cl.
    *A61F 2/44* (2006.01)
    *A61B 17/16* (2006.01)
    *A61B 17/17* (2006.01)
    *A61B 17/34* (2006.01)
    *A61B 17/88* (2006.01)
    *A61B 19/00* (2006.01)
    *A61F 2/46* (2006.01)
    *A61F 2/28* (2006.01)
    *A61F 2/30* (2006.01)

(52) U.S. Cl.
    CPC ............... *A61F2002/30225* (2013.01); *A61F 2002/30285* (2013.01); *A61F 2002/30774* (2013.01); *A61F 2002/30825* (2013.01); *A61F 2002/30892* (2013.01); *A61F 2002/30904* (2013.01); *A61F 2002/4475* (2013.01); *A61F 2002/4624* (2013.01); *A61F 2002/4625* (2013.01); *A61F 2002/4629* (2013.01); *A61F 2310/00017* (2013.01); *A61F 2310/00023* (2013.01); *A61F 2310/00029* (2013.01)

(56) References Cited

U.S. PATENT DOCUMENTS

| | | | |
|---|---|---|---|
| 5,944,658 | A | 8/1999 | Koros et al. |
| 7,494,463 | B2 | 2/2009 | Nehls |
| 7,615,079 | B2 | 11/2009 | Flickinger et al. |
| 7,666,201 | B2 | 2/2010 | Grayzel et al. |
| 8,449,463 | B2 * | 5/2013 | Nunley et al. ............ 600/227 |
| 2003/0149341 | A1 | 8/2003 | Clifton |
| 2004/0230191 | A1 | 11/2004 | Frey et al. |
| 2005/0149035 | A1 | 7/2005 | Pimenta et al. |
| 2005/0216088 | A1 | 9/2005 | McKinley et al. |
| 2006/0084844 | A1 | 4/2006 | Nehls |
| 2006/0247645 | A1 | 11/2006 | Wilcox et al. |
| 2006/0287730 | A1 | 12/2006 | Segal et al. |
| 2008/0021284 | A1 | 1/2008 | Hestad et al. |
| 2008/0183046 | A1 | 7/2008 | Boucher et al. |
| 2008/0262501 | A1 | 10/2008 | Chen et al. |
| 2009/0036746 | A1 | 2/2009 | Blackwell et al. |
| 2009/0228110 | A1 | 9/2009 | McClintock |
| 2010/0130827 | A1 | 5/2010 | Pimenta et al. |
| 2010/0174146 | A1 | 7/2010 | Miles et al. |

OTHER PUBLICATIONS

Japanese Unexamined Patent Application Publication No. 2007-512853.
Japanese Unexamined Patent Application Publication No. 2010-510841.
Japanese Office Action dated Aug. 4, 2015 in connection with corresponding Japanese Patent Application No. 2013-533013.
Australian Patent Examination Report dated Aug. 17, 2015 in connection with corresponding Australian Patent Application No. 2014203469.

* cited by examiner

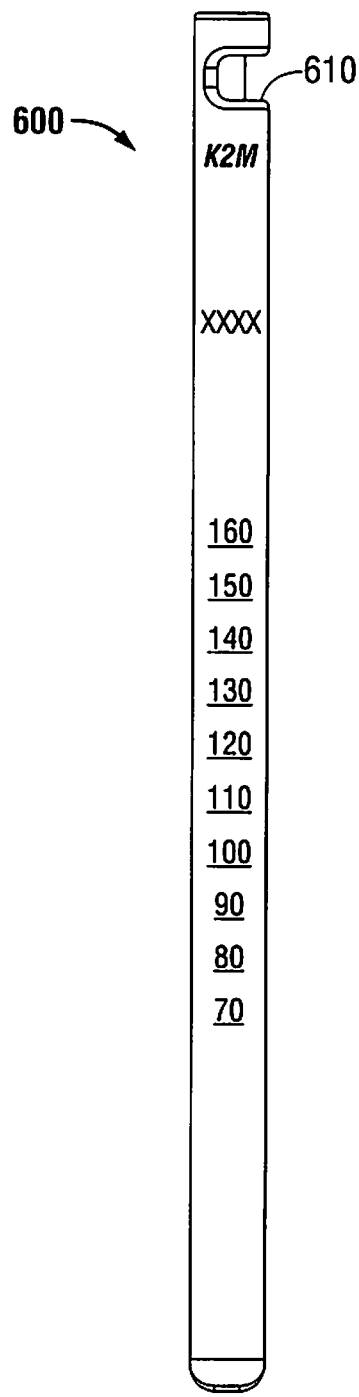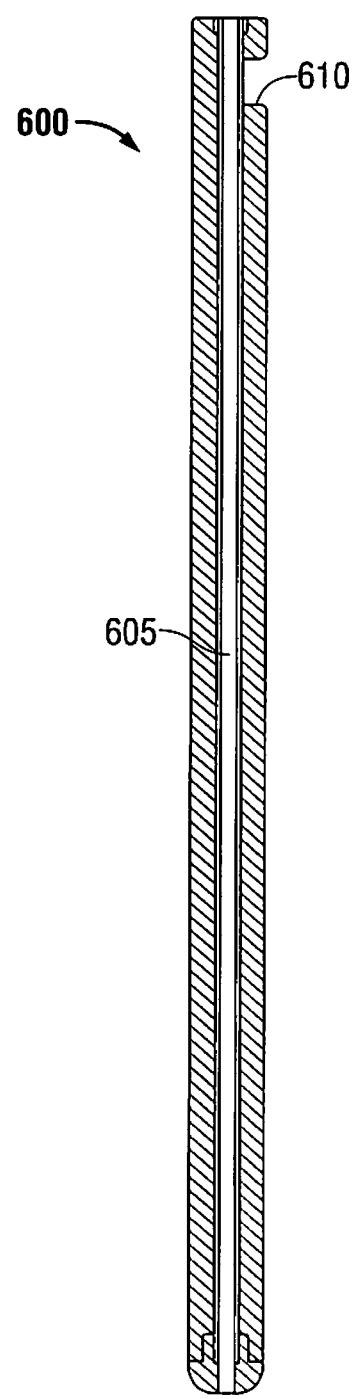
FIG. 9C  FIG. 9D

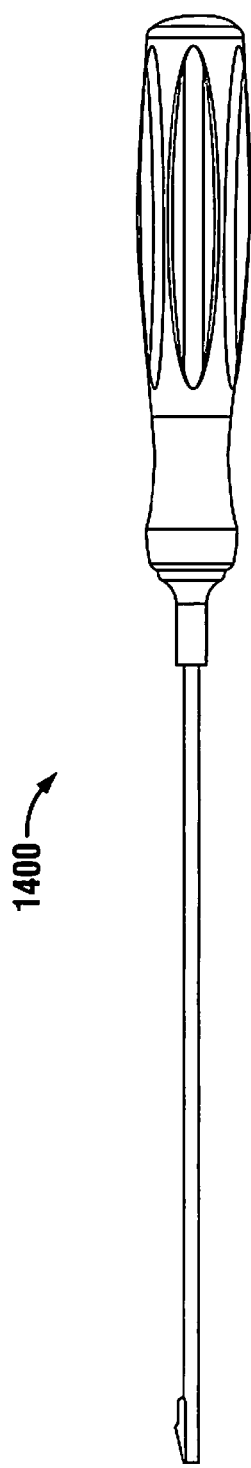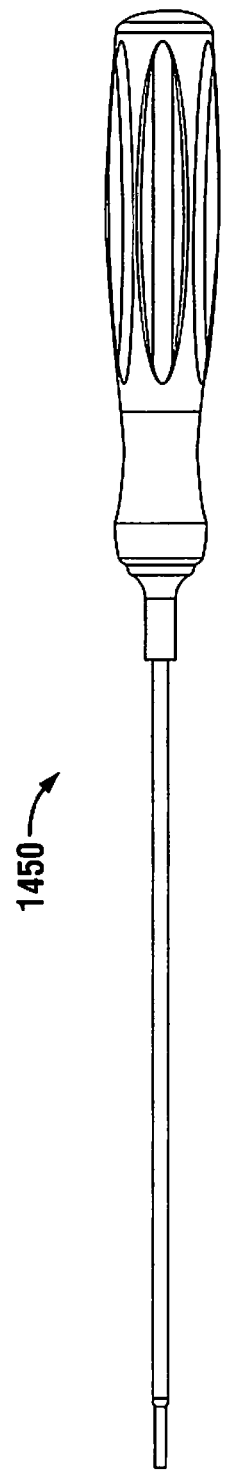

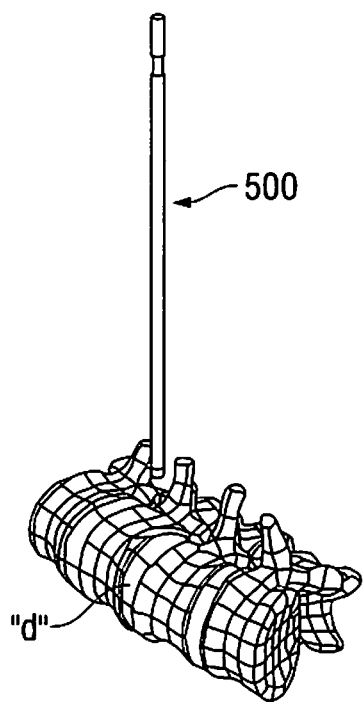 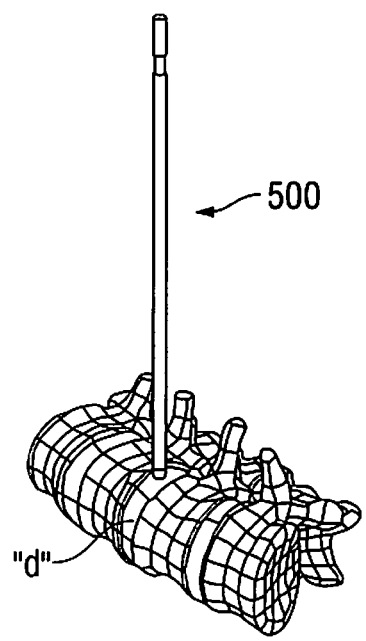
FIG. 24  FIG. 25

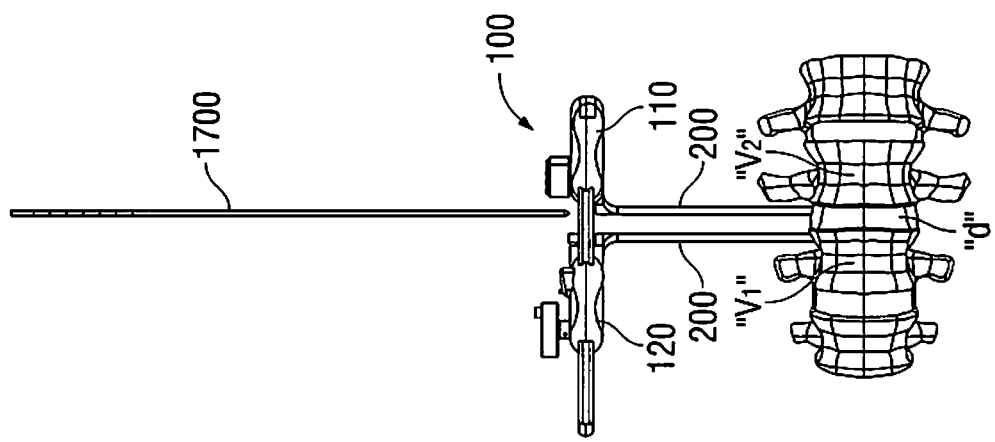
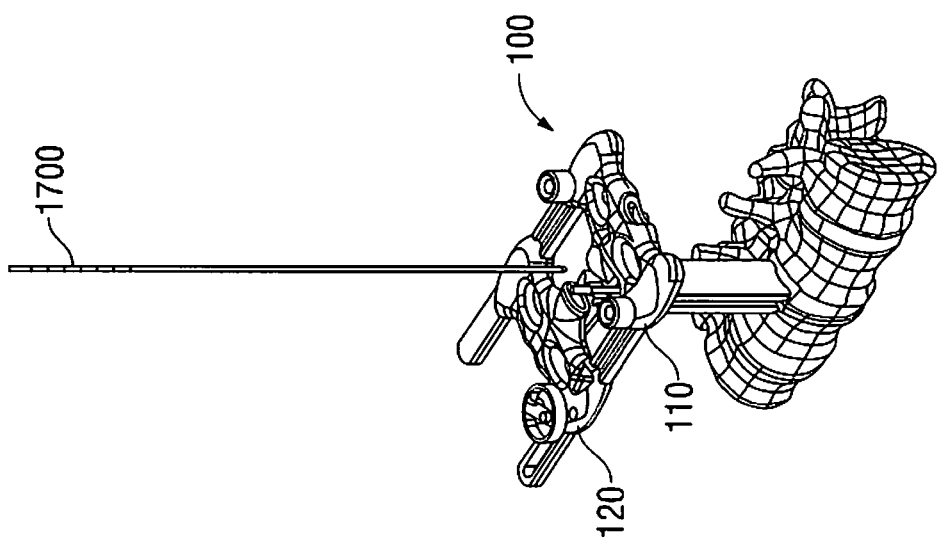

LATERAL ACCESS SYSTEM AND METHOD OF USE

CROSS REFERENCE TO RELATED APPLICATIONS

This application is a continuation of U.S. patent application Ser. No. 13/270,588, filed Oct. 11, 2011, which claims priority to, and the benefit of, U.S. Provisional Patent Application Ser. No. 61/391,402, filed Oct. 8, 2010, the entire contents of each of which are incorporated by reference herein.

BACKGROUND

1. Technical Field

The present disclosure is related to devices used in accessing a spinal work location. More particularly, the present disclosure relates to devices and methods for laterally accessing a spinal work location

2. Background of Related Art

Disease, the effects of aging, or physical trauma resulting in damage to the spine has been treated in many instances by fixation or stabilization of the effected vertebra. A wide variety of spinal fixation apparatuses have been employed in surgical procedures for correcting spinal injuries and the effects of spinal diseases.

After a partial or complete discectomy, the normally occupied space between adjacent vertebral bodies is subject to collapse and/or misalignment due to the absence of all or a part of the intervertebral disc. In such situations, the physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. As is typical, the intervertebral spaces are accessed either anteriorly or posteriorly. It would be desirable to access the intervertebral spaces via a lateral approach.

SUMMARY

In accordance with an embodiment of the present disclosure, there is provided a surgical access device including a frame having first and second arms, first and second supports, and first and second retractor blades. In particular, the first support is releasably coupled with the first and second arms, and the second support is slidably mounted on the first and second arms. The second support is movable between a first position with the retractor blades in close cooperative alignment and a spaced apart position with respect to the first support. The first and second retractor blades are releasably coupled with the first and second supports, respectively, wherein the first and second retractor blades each have a distal end portion configured and adapted to engage a vertebral body.

In an embodiment, the distal end portion of the respective first and second retractor blades may define a recess configured and adapted to engage the vertebral body. In addition, the recess defined in the respective distal end portions of the first and second retractor blades may include an arcuate portion having a radius of curvature substantially identical to that of the vertebral body.

The first and second retractor blades may each define a longitudinal groove, whereby when the first and second retractor blades are in a close cooperative position the grooves define a lumen. Moreover, the longitudinal groove may be configured and dimensioned to receive therethrough a fixation pin or guide wire.

In another embodiment, the first and second arms may each define a longitudinal cavity defined along the length of the first and second arms. The second support may include a translation knob configured to move the second support to a particular position along the first and second arms. The surgical access device may further include an auxiliary blade transversely mounted on one of the first and second arms. In addition, the surgical access device may further include a locking wheel configured and adapted to secure the auxiliary blade to a particular position along one of the first and second arms. The auxiliary blade may be transversely adjustable.

The second support may include a ratchet assembly configured and adapted to provide a uni-directional movement of the second support along the first and second arms. The retractor blade may include an engaging portion and a blade portion extending from the engaging portion. The engaging portion may be configured and adapted to engage an underside of the respective first and second support. The engaging portion of the retractor blade may also include a protruding portion configured and dimensioned to be received through a cavity defined in respective first and second supports.

In accordance with another aspect of the present disclosure, there is provided a method of accessing the spine. The method includes providing a surgical access system including a retractor device, a dissector, a spinal implant, a guide wire, and a fixation pin. In particular, the retractor device includes first and second supports and first and second retractor blades. In particular, the second support is movable between a close cooperative position and a spaced apart position with respect to the first support. The first and second retractor blades are releasably coupled with the first and second supports, respectively, wherein the first and second retractor blades each have a distal end portion configured and adapted to engage a vertebral body. The method further includes establishing a path to the spine, introducing the first and second retractor blades through the path, in one orientation with the retractor blades in close cooperative alignment, reorienting the retractor to a second orientation, retracting open the retractor device to separate the second support from the first support, thereby separating the retractor blades mounted to the supports to retract tissue, inserting a fixation pin into a vertebral body to maintain blade position relative to the vertebral body, and performing surgery through the operating channel defined by the retracted blades. The surgery may include positioning a spinal implant between vertebral bodies.

In an embodiment, introducing the retractor blades through the incision may include placing the first and second retractor blades in close cooperative alignment. Establishing an adequate path to the spine may include inserting a dissector to the disc and inserting the guide wire through the dissector into the disc space.

The method may further include distracting the disc utilizing a disc spreader. In addition, the method may also include inserting the retractor with the blades in close cooperative alignment and oriented along the axis of the fibers of the psoas muscle, and rotating the retractor device so that the orientation of the retractor blades is in line with the endplates of the vertebrae and substantially transverse to the fibers of the psoas muscle. Rotating the retractor device may include rotating the retractor device to a position in which the distal portion of at least one of the retractor blades conforms to and contacts the vertebral body.

In another embodiment, the distal end portions of the respective first and second retractor blades may define a concave recess configured and adapted to engage the vertebral body. The recess defined in the distal end portions of the respective first and second retractor blades may include an arcuate portion having a radius of curvature substantially identical to that of the vertebral body, so that when the retractor blades are oriented transverse to the psoas muscle the arcuate distal end portion of each blade substantially conforms to and may be positioned against the arcuate lateral wall of the corresponding vertebra.

The first and second retractor blades may each define at least one longitudinal groove, whereby when the first and second retractor blades are positioned in close cooperative alignment the grooves define a lumen. The longitudinal groove may be configured and dimensioned to receive therethrough a fixation pin. The retractor device may further include an auxiliary blade transversely mounted on one of the first and second retractor blades. In particular, the auxiliary blade may include a longitudinal groove. The dissector may include indicia thereon marking the distance from a distal end of the dissector.

The method may further include forming a lateral incision, digitally probing the retroperitoneal space, inserting one or more dissectors to loosen tissue and form a lateral pathway to the disc space, inserting a guide wire or pin through a dissector into the disc space, removing the dissector, and mounting the retractor over the guidewire or pin by inserting the guidewire or pin through a lumen defined by longitudinal grooves in one or both of the first and second retractor blades. With the blades in close cooperative alignment, the retractor blades are inserted over the guidewire through tissue with the blades oriented in a first position along or substantially parallel to the longitudinal axis of the psoas muscle until the distal end of the retractor blades are adjacent the disc space. The blades when positioned in close approximation are substantially flat and capable of dividing the fibers of the psoas muscle during insertion of the blades through the muscle. The substantially flat profile of the retractor blades when in close approximation obviates the need to insert the retractor over any type of introducer structure, such as a dissector. The retractor is rotated to a second position substantially transverse to the first position to orient the retractor blades substantially transverse to the psoas muscle with a first retractor blade adjacent a first vertebral body. The distal end of the first retractor blade conforms to the vertebral body lateral surface. Optionally, one or more fixation pins are inserted through the lumen formed by grooves in one or both blades and driving or screwing the fixation pin laterally into the vertebral body to fix the position of the first blade with respect to the vertebral body. The second blade is moved away from the first blade to form a gap between the blades which spans the disc space, so that the second blade is adjacent a second, adjacent vertebral body across the disc space with the distal end of the second retractor blade conforming to the shape of the second vertebral body. Optionally, a second fixation pin is driven or screwed into the second vertebral body to fix the position of the second blade relative to the second vertebral body, thereby defining an operating channel extending from the skin to the disc space. Surgery on the disc space may be performed through the operative channel (which surgery may include removing disc material and inserting bone or a synthetic implant in the interbody space), subsequent to which the optional fixation pins, if used, may be removed, the retractor withdrawn and the incision closed in a traditional manner. Advantageously, the retractor defines a clear open channel unobstructed by parts of the retractor or instruments, which provides good visibility to the disc space visually and under imaging such as fluoroscopy.

The method may further include introducing an intradiscal shim through the groove of the auxiliary blade and into the disc space. The method may also include determining a blade length of the first and second retractor blades. In addition, the method may also include placing a patient in a lateral decubitus position on an operating table.

In still another embodiment, retracting open the retractor device may include positioning the second support in the spaced apart position with respect to the first support. In addition, inserting the fixation pin into the vertebral body may include inserting the fixation pin through the longitudinal groove of the respective first and second retractor blades.

BRIEF DESCRIPTION OF THE DRAWINGS

Various embodiments of the present disclosure are described hereinbelow with reference to the drawings, wherein:

FIG. 9C is a side view of another dissector for use with the retractor system of FIG. 1;

FIG. 9D is a side cross-sectional view of the dissector of FIG. 9C;

FIG. 17 is a side view of an intradiscal shim inserter for use with the intradiscal shim of FIG. 16;

FIG. 18 is a side view of an intradiscal shim extractor for use with the intradiscal shim of FIG. 16;

FIGS. 24 and 25 are perspective views of the dissector of FIG. 9A illustrating use thereof;

FIGS. 37 and 38A are perspective views of the retractor system of FIG. 36A illustrating removal of the guide wire;

FIG. 38B is a side view of the retractor system of FIG. 38A;

DETAILED DESCRIPTION OF EMBODIMENTS

Figure 1:
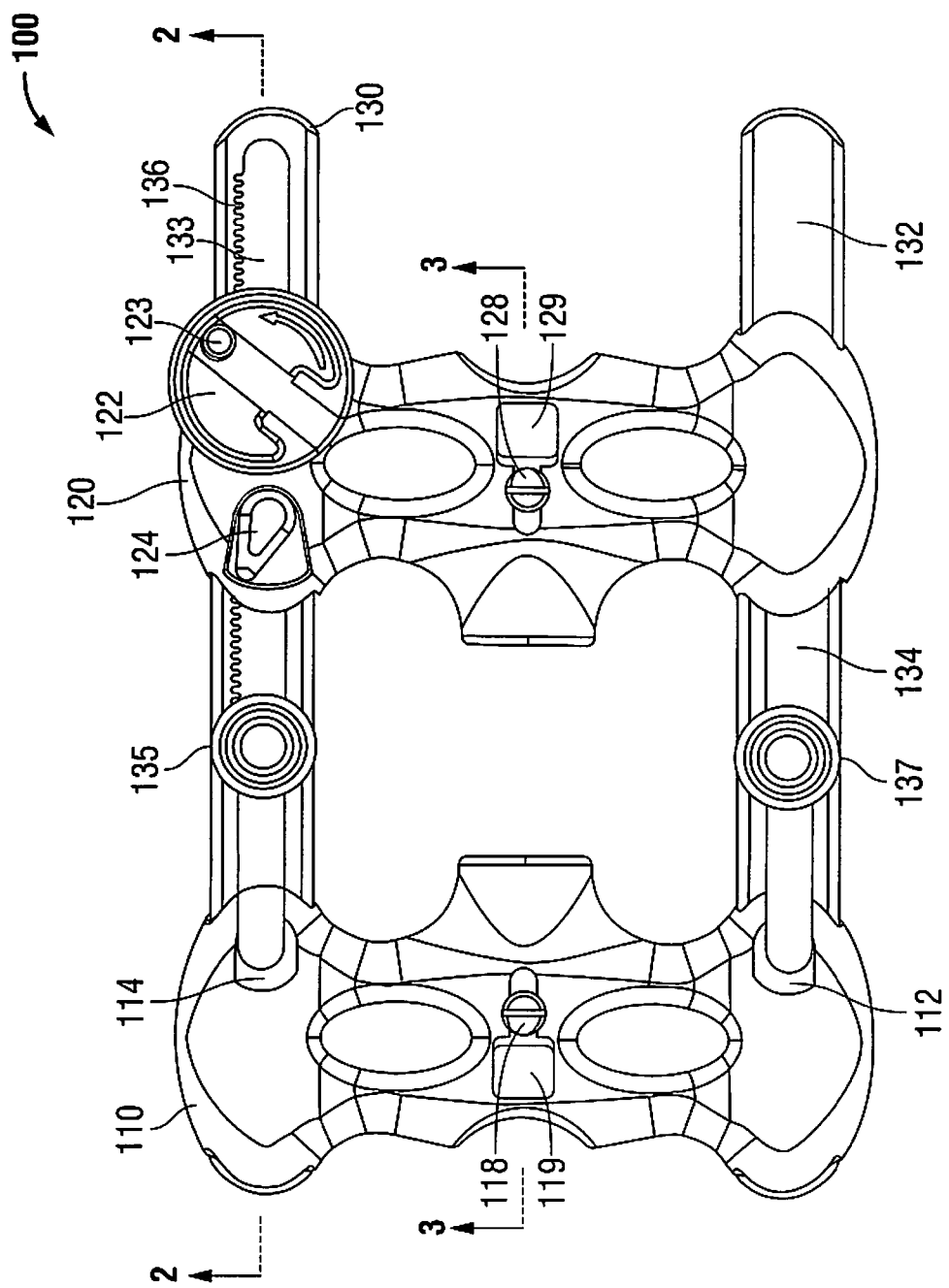
FIG. 1 is a top, plan view of a retractor system in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

Figure 2:
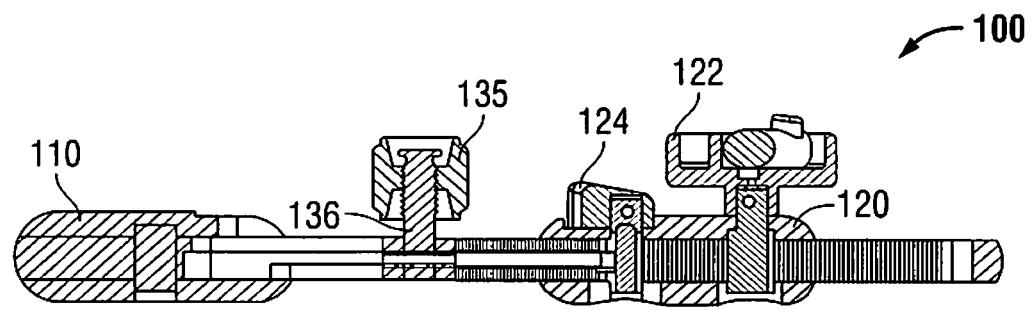
FIG. 2 is a side cross-sectional view of the retractor system of FIG. 1 cut along a section line of 2-2 in FIG. 1.
Figure 3:
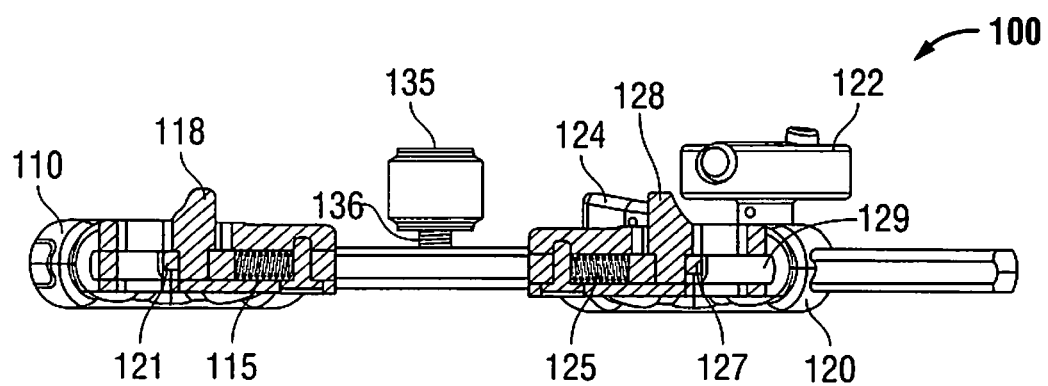
FIG. 3 is a side cross-sectional view of the retractor system of FIG. 1 cut along a section line of 3-3 in FIG. 1.

With reference to FIGS. 1-3, an embodiment of the present disclosure is shown generally as a retractor system 100 configured and adapted for a minimally invasive surgical procedure to access, for example, the thoracic or lumbar vertebrae. Retractor system 100 includes a first support 110 having arms 130, 132 extending therefrom and a second support 120 that is slidably mounted on arms 130, 132. Second support 120 may be secured in a plurality of locations relative to first support 110. Each support 110, 120 is configured and dimensioned to receive and support a retractor blade 200 (FIGS. 4-6) releasably secured thereto, as will be discussed in detail hereinbelow. Movement of second support 120 along arms 130, 132 allows retractor blade 200 on second support 120 to be moved between a position closely adjacent to a blade mounted to support 110, and a spaced apart position with respect to the opposing retractor blade 200 releasably secured with first support 110.

With particular reference to FIG. 1, each arm 130, 132 is coupled to first support 110. Arms 130, 132 define respective cavities 133, 134 that extend at least partially along the length of respective arms 130, 132. Cavity 133 of arm 130 includes a portion having teeth 136 that operatively engage a translation knob 122 of second support 120. Translation knob 122 is configured and adapted to secure second support 120 to a particular location on arm 130 upon rotation of translation knob 122. In addition, each cavity 133, 134 is configured and dimensioned to accommodate locking wheels 135, 137 translatably disposed in respective cavities 133, 134. Each locking wheel 135, 137 is configured and adapted to secure auxiliary blades 400 (FIG. 7) at a position along respective arms 130, 132, as will be described hereinbelow. While only cavity 133 is illustrated with teeth to interact with a wheel and ratchet of the second support, alternatively or in addition there could be teeth associated with cavity 134 to engage a ratchet and/or wheel on the other side of secondary support 120.

Retractor blade 200 is releasably attachable to first support 110. An engaging portion 202 (FIG. 4) of retractor blade 200 engages an underside of first support 110. Moreover, first support 110 defines a cavity 119 configured and dimensioned to detachably secure a protruding portion 204 (FIG. 4) of retractor blade 200 therein. In addition, first support 110 includes a locking slider 118 that slidably engages protruding portion 204 of retractor blade 200 to releasably secure protruding portion 204 of retractor blade 200 within cavity 119. Locking slider 118 is operatively coupled to a biasing member 115 (FIG. 3) such that locking slider 118 is biased toward a locked state. An engaging portion 121 (FIG. 3) of locking slider 118 engages a groove 206 (FIG. 4) defined in protruding portion 204. In this manner, retractor blade 200 is releasably secured to first support 110.

With continued reference to FIG. 1, first support 110 further defines a pair of recessed portions 112, 114 aligned with cavities 133, 134, respectively. Recessed portions 112, 114 are configured and dimensioned to accommodate therein respective locking wheels 135, 137 to enable approximation of first and second supports 110, 120 to a close cooperative position with locking wheels 135, 137 nested in the recessed portions.

Second support 120 includes similar features of first support 110. In particular, second support 120 defines a cavity 129 configured and dimensioned to receive protruding portion 204 of retractor blade 200. Second support 120 also includes a locking slider 128 configured and adapted to releasably secure protruding portion 204 in cavity 129. As discussed hereinabove with respect to locking slider 118, locking slider 128 is operatively coupled to a biasing member 125 (FIG. 3), whereby locking slider 128 is biased toward the engaging state. In the engaging state, an engaging portion 127 (FIG. 3) of locking slider 128 at least partially protrudes through cavity 129, whereby when protruding portion 204 of retractor blade 200 is disposed in cavity 129, engaging portion 127 of locking slider 128 engages groove 206 defined in protruding portion 204. In this manner, retractor blade 200 is releasably secured with second support 120.

In contrast to first support 110, second support 120 includes a translation knob 122 rotatably mounted on second support 120 to move second support 120 to a particular position along the length of arms 130, 132. Translation knob 122 engages teeth 136 on arm 130, whereby rotation of translation knob 122 moves second support 120 to a particular position along arm 130. A ratchet engages the teeth as the second support is moved away from the first support to secure the second support position relative to arms 130, 132, and hence also relative to the first support. Rotation of translation knob 122 in the opposite direction with the ratchet released moves the second support 120 along arm 130 in the opposite direction toward the first support. In addition, second support 120 includes a ratchet assembly configured to enable uni-directional movement of second support 120 and lock the second support in position along arms 130, 132. The ratchet assembly includes a ratchet knob 124 that is configured to release/disengage the ratchet assembly with arm 130 to enable selective uni-directional movement of second support 120.

Figure 4:
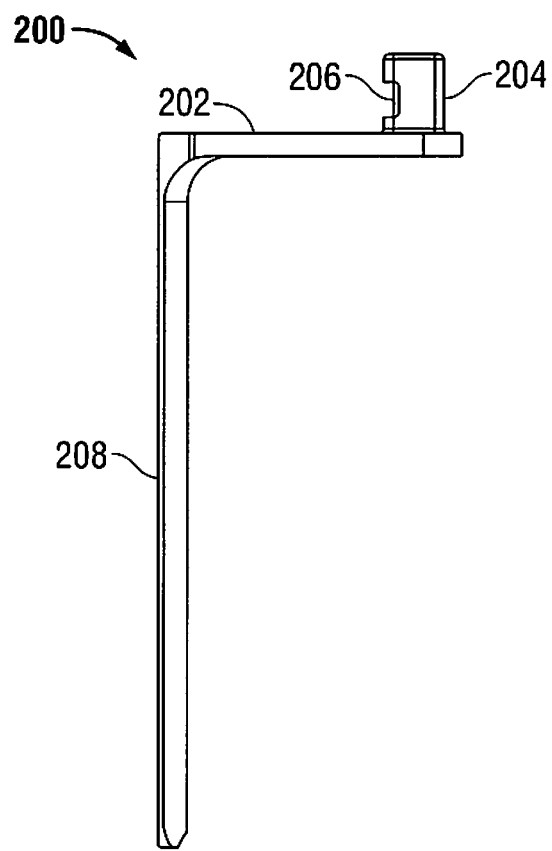
FIG. 4 is a side view of a retractor blade for use with the retractor system of FIG. 1.
Figure 5:
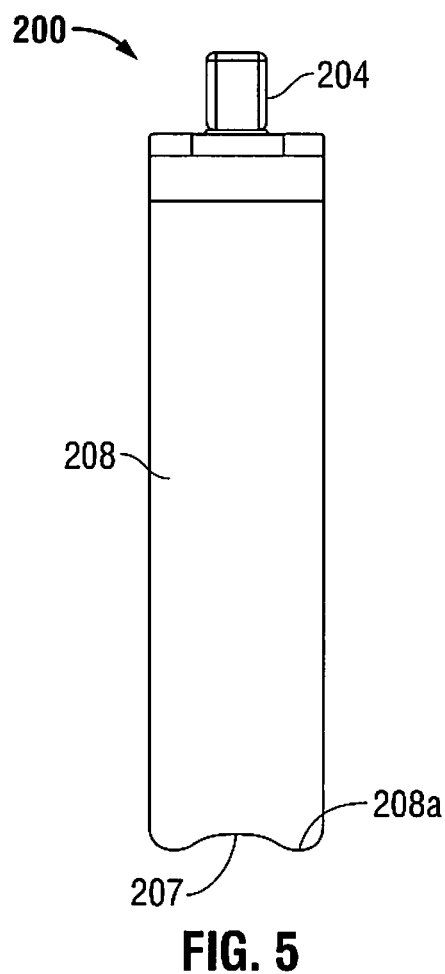
FIG. 5 is a front view of the retractor blade of FIG. 4 for use with the retractor system of FIG. 1.
Figure 6:
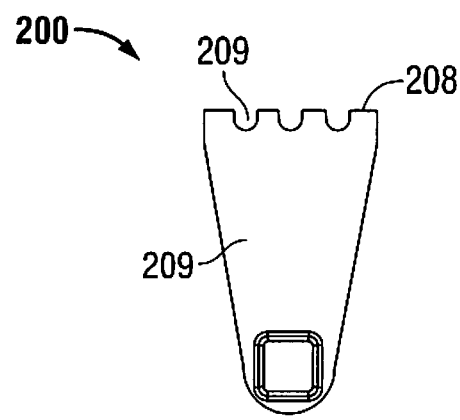
FIG. 6 is a top, plan view of the retractor blade of FIG. 4 for use with the retractor system of FIG. 1.
Figure 32A:
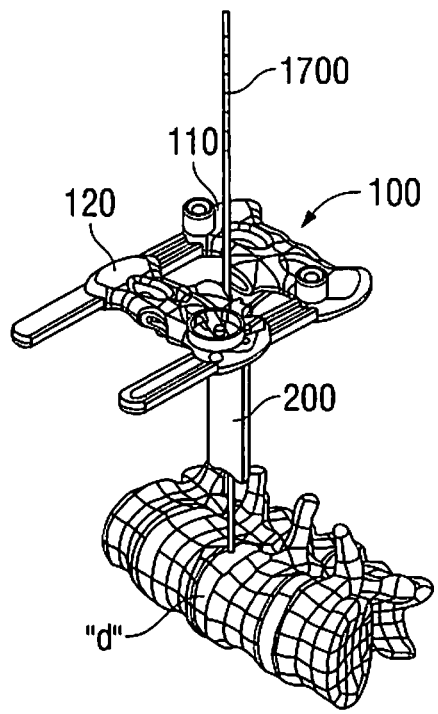
FIG. 32A is a perspective view of the retractor system of FIG. 1 including the retractor blades of FIG. 4 attached thereto illustrating insertion of the retractor system over the guide wire.
Figure 32B:
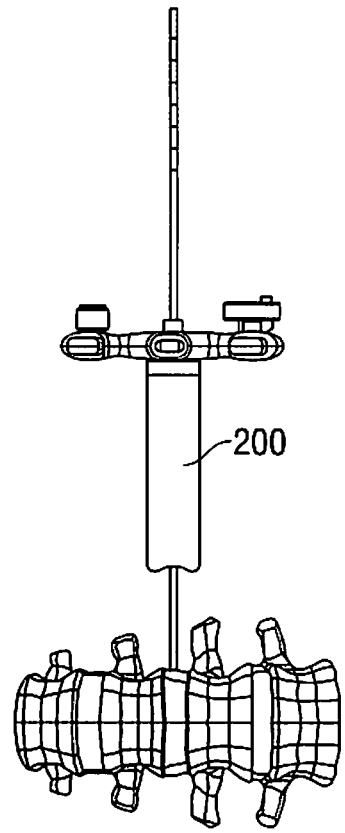
FIG. 32B is a side view of the retractor system of FIG. 32A.
Figure 32C:
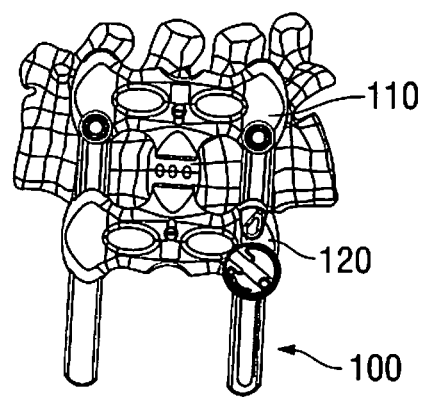
FIG. 32C is a top view of the retractor system of FIG. 32A.

With reference now to FIGS. 4-6, retractor blade 200 is releasably and interchangeably attachable to first or second supports 110, 120, and includes engaging portion 202 and a blade portion 208 extending therefrom. Engaging portion 202 engages the underside of respective first and second supports 110, 120 in a superposed relation. Blade portion 208 is substantially orthogonal to engaging portion 202, whereby when retractor blade 200 is releasably secured with respective first and second supports 110, 120, blade portion 208 is substantially orthogonal to first and second supports 110, 120. However, it is further contemplated that each retractor blade 208 may define a predetermined fixed angle with respect to engaging portion 202 and first and second supports 110, 120. In use, retractor blades 200 are attached to first and second supports 110, 120, respectively, as shown in FIGS. 32A and 32B. As best seen in FIG. 4, the retractor blade has a thin, substantially flat profile.

With reference to FIG. 4, engaging portion 202 includes a protruding portion 204 configured and dimensioned to extend through respective cavities 119, 129 of first and second supports 110, 120. In particular, each protruding portion 204 defines a groove 206 configured and dimensioned to securely engage respective engaging portions 121, 127 (FIG. 3) of locking sliders 118, 128 of first and second supports 110, 120.

Figure 23:
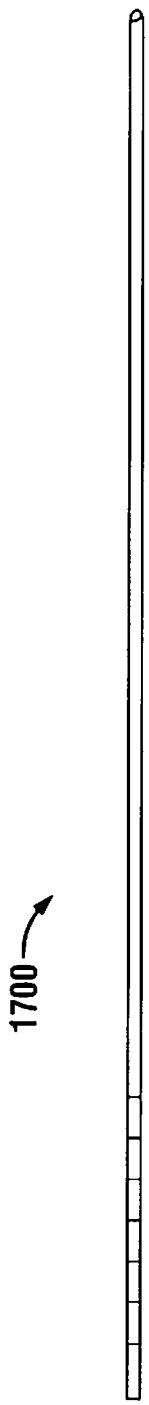
FIG. 23 is a side view of a guide wire for use with the retractor system of FIG. 1.

With particular reference to FIG. 6, each blade portion 208 of retractor blade 200 includes one or more longitudinal channels 209 extending substantially along the length of blade portion 208. Thus, when retractor blades 200 of respective first and second supports 110, 120 are in close cooperative alignment, opposing channels 209 of blades portions 208 define one or more lumens for receiving, for example, a guide wire 1700 (FIG. 23), a guide pin, or other surgical implement therethrough. The groove may be rounded and may have slightly greater than a 180° circumference so that a pin inserted into the groove is held in place, although the pin may be pulled out of the groove with sufficient force.

Figure 40A:
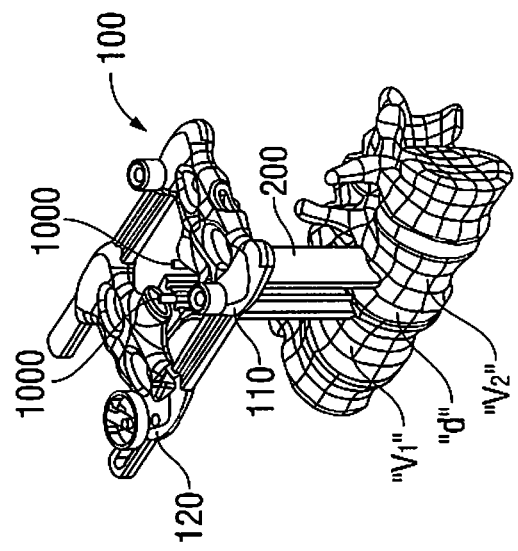
FIG. 40A is a perspective view of the retractor system of FIG. 39A illustrating the retractor system providing access and visualization of the disc.
Figure 40B:
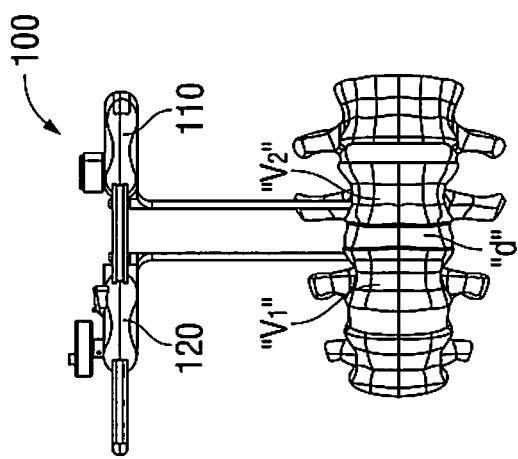
FIG. 40B is a side view of the retractor system of FIG. 40A.

With particular reference back to FIG. 5, a distal end portion 208a of blade portion 208 defines a recess 207 having a concave profile. The concave profile of recess 207 is adapted to engage and accommodate the contour of a vertebral body. Optimally, the concave recess defines a radius of curvature in the range of about 0.1 inch to about 1.0 inch, and more preferably about 0.6 inch. The concave profile of recess 207 improves engagement of retractor blade 200 with the vertebral body (see, for example, FIG. 40A) and, for example, reduces slippage therewith and tissue creeping under and around the blade, especially as the retractor is manipulated during surgery. The surgeon may be provided with a plurality of retractor blades having various radii of curvatures of concave profile of the recess defined in a distal portion of the blade portion to accommodate various contours of the vertebral body.

Figure 7:
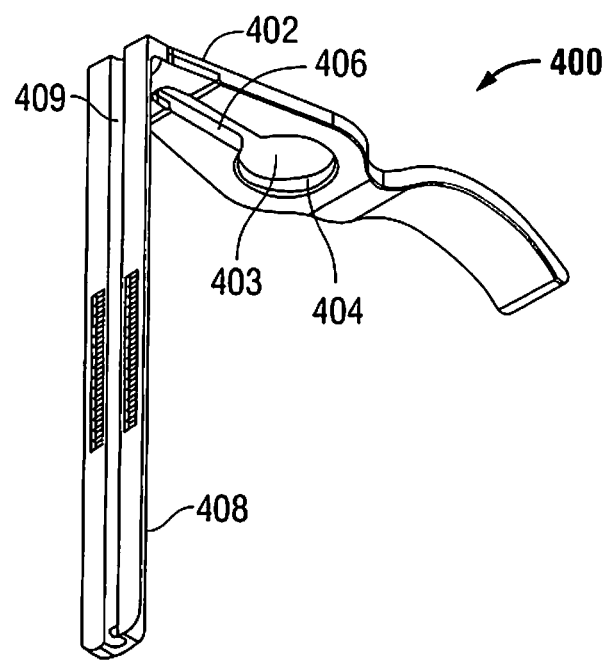
FIG. 7 is a perspective view of an auxiliary blade for use with the retractor system of FIG. 1.
Figure 16:
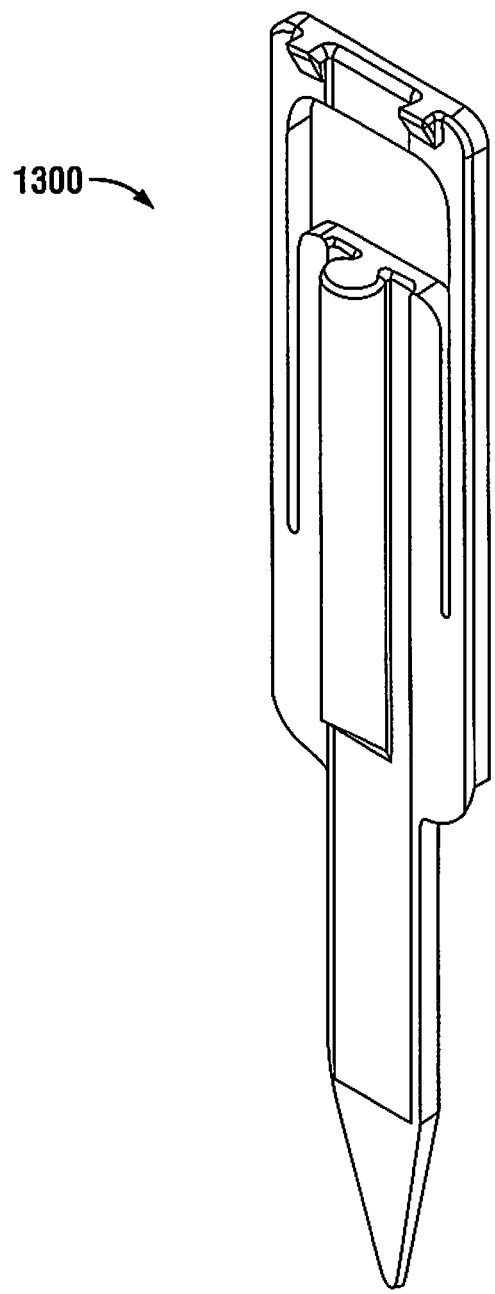
FIG. 16 is a perspective view of an intradiscal shim for use with the retractor system of FIG. 1.

With reference to FIGS. 1 and 7, movement of second support 120 along arms 130, 132 from a close cooperative position with first support 110 to a space apart position from first support 110 allows retraction of tissue in the longitudinal direction. However, further retraction in the transverse direction can be achieved through the use of an auxiliary blade 400 (FIG. 7). Auxiliary blade 400 includes an engaging portion 402 defining a cavity 403 of varying dimensions and a blade portion 408 extending from engaging portion 402. Cavity 403 of engaging portion 402 is configured and dimensioned to be secured along the length of arms 130, 132. Specifically, cavity 403 defines an enlarged portion 404 and a narrowed portion 406. In particular, enlarged portion 404 of cavity 403 is dimensioned to receive therethrough locking wheel 135, 137 such that engaging portion 402 of auxiliary blade 400 may be positioned on arms 130, 132 in a superposed relation and secured by locking wheels 135, 137. A neck portion 136 (FIG. 3) of locking wheel 135, 137 is configured and dimensioned to be slidably received in narrowed portion 406 of auxiliary blade 400. Blade portion 408 is substantially orthogonal with respect to engaging portion 402, whereby when auxiliary blade 400 is secured with respective arms 130, 132, blade portion 408 is substantially orthogonal to arms 130, 132. In addition, each blade portion 408 includes one or more longitudinal channels 409 extending substantially along the length of blade portion 408. Channels 409 are configured and dimensioned to receive, for example, guide wire 1700, a guide pin, or other surgical implement such as an intradiscal shim 1300 (FIG. 16), as discussed below.

Under such configuration, auxiliary blade 400 may be adjustably secured to arms 130, 132. Specifically, neck portion 136 of locking wheel 135 may be slidably received through narrowed portion 406 of cavity 403 to enable the surgeon to select a particular position of auxiliary blade 400 in the transverse direction, as well as the longitudinal direction on arms 130, 132. Upon selecting a desirable position, the surgeon may rotate locking wheel 135, 137 in a first direction to secure auxiliary blade 400 to arm 130, 132. The surgeon may rotate locking wheel 135, 137 in a direction opposite the first to release auxiliary blade 400 from arm 130, 132.

With reference now to FIGS. 9A-9F, there are illustrated dissectors 500, 600, 700 having various sizes configured for use with retractor system 100. Each dissector 500, 600, 700 has a central passage 505, 605, 705 extending along its length with open proximal and distal ends. Central passage 505, 605, 705 is configured and dimensioned such that dissector 500, 600, 700 may slidably receive guide wire 1700 (FIG. 23) or guide pin therethrough. Guide wire 1700 or guide pin may guide dissector 500, 600, 700 to slide therealong, as will be described below. In addition, each dissector 500, 600, 700 has indicia indicating depth of the body cavity or the distance between the epidermal tissue surface and the vertebral body. The surgeon may utilize such indicia to select an appropriate retractor blade. In one embodiment, central passage 505, 605, 705 is defined by an electrically conductive tube with plastic over molded onto and surrounding the tube. A notch 610, 710 is formed in the proximal portion of dissector 600, 700 to expose a portion of the tube should a surgeon desire to use dissector 600, 700 in association with an electromyography system in a known manner. A clip from the electromyography system can be contacted with the conductive tube at the proximal notch, with the signal transmitted along the tube inside the insulating plastic outer body, to the distal tip of the conductive tube which contacts tissue.

Figure 10:
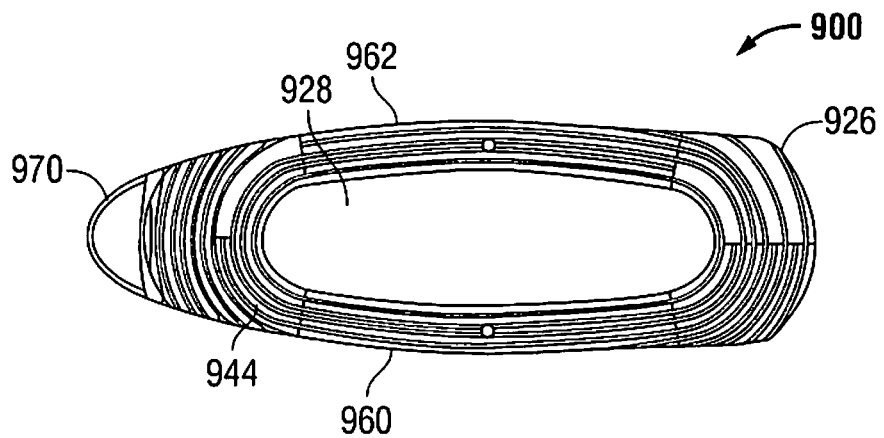
FIG. 10 is a top, plan view of a spinal interbody spacer for use with the retractor system of FIG. 1.
Figure 11:
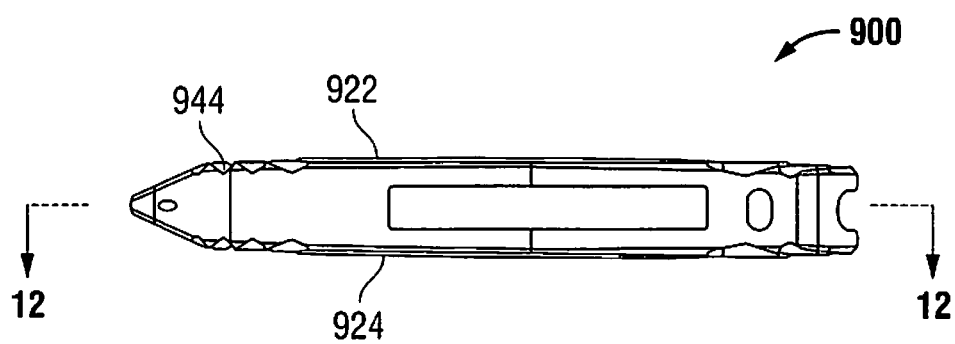
FIG. 11 is a side view of the spinal interbody spacer of FIG. 10.
Figure 12:
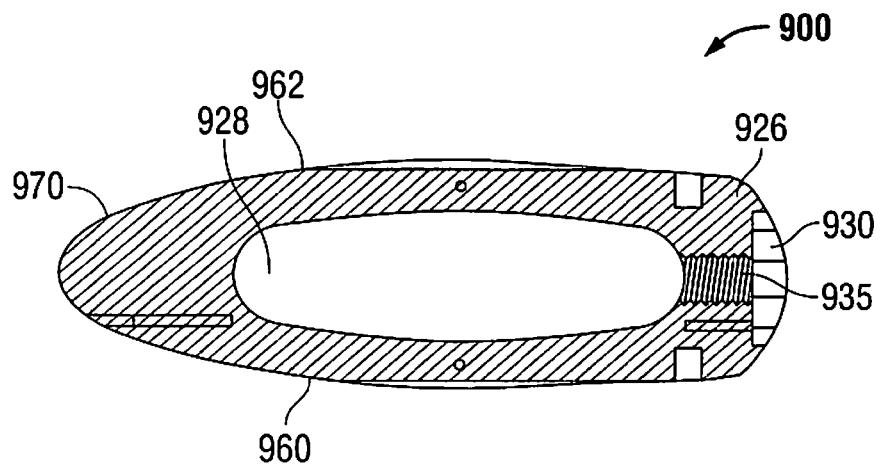
FIG. 12 is a cross-sectional view of the spinal interbody spacer of FIG. 10 cut along a section line 12-12 in FIG. 11.

With reference now to FIGS. 10-12, there is illustrated a spinal interbody spacer 900 for use with retractor system 100 for placement between vertebrae. Spacer 900 includes a pair of opposing sidewalls 960, 962, a blunt nose 970, and an arcuate proximal wall 926. Spacer 900 is monolithically formed and is made of any suitable biocompatible material such as polyetheretherketone (PEEK), polysulfone (RADEL), polyetherimide (ULTEM), stainless steel, cobalt chrome, titanium, and titanium alloys.

Interbody spacer 900 defines a generally torpedo-shaped profile with an opening 928 extending therethrough to permit bone growth between adjacent vertebrae. In addition, opening 928 may contain additional bone graft material. Blunt nose 970 includes substantially contoured, tapered surface to facilitate insertion thereof between the vertebral bodies. Spacer 900 includes vertebral body engaging top and bottom surfaces 922, 924 having protrusions configured to facilitate gripping and securing of spacer 900 with adjacent vertebra. In particular, the protrusion includes ring-patterned protrusions 944 concentrically arranged with respect to opening 928. In addition, ring-patterned protrusions 944 of opposing top and bottom surfaces 922, 924 may be configured to enable secure engagement with respect to each other when disposed in a superposed relation.

Figure 13A:
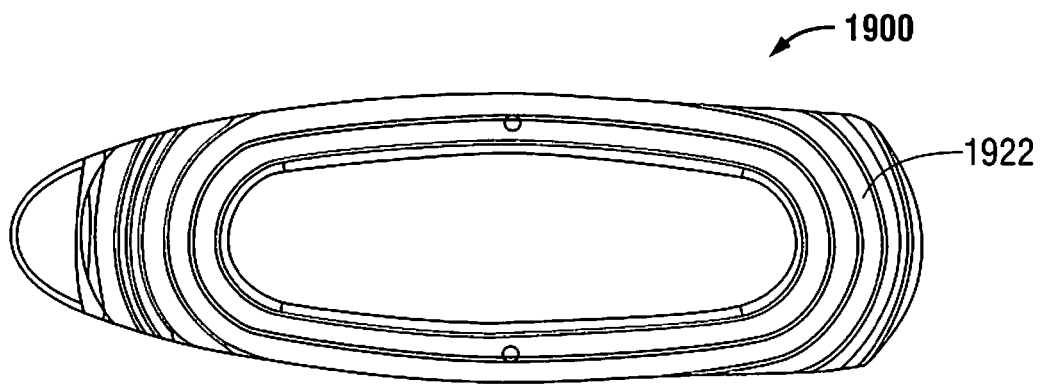
FIG. 13A is a top, plan view of another embodiment of a spinal interbody spacer for use with the retractor system of FIG. 1.
Figure 13B:
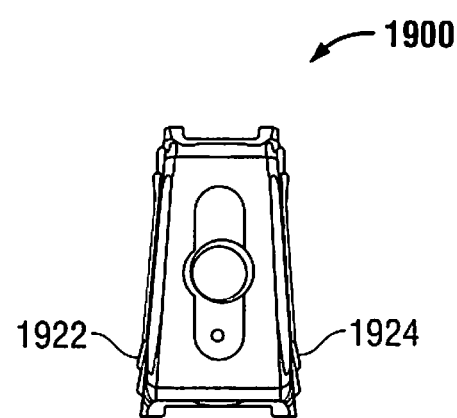
FIG. 13B is a rear view of the spinal interbody spacer of FIG. 13A.
Figure 14:
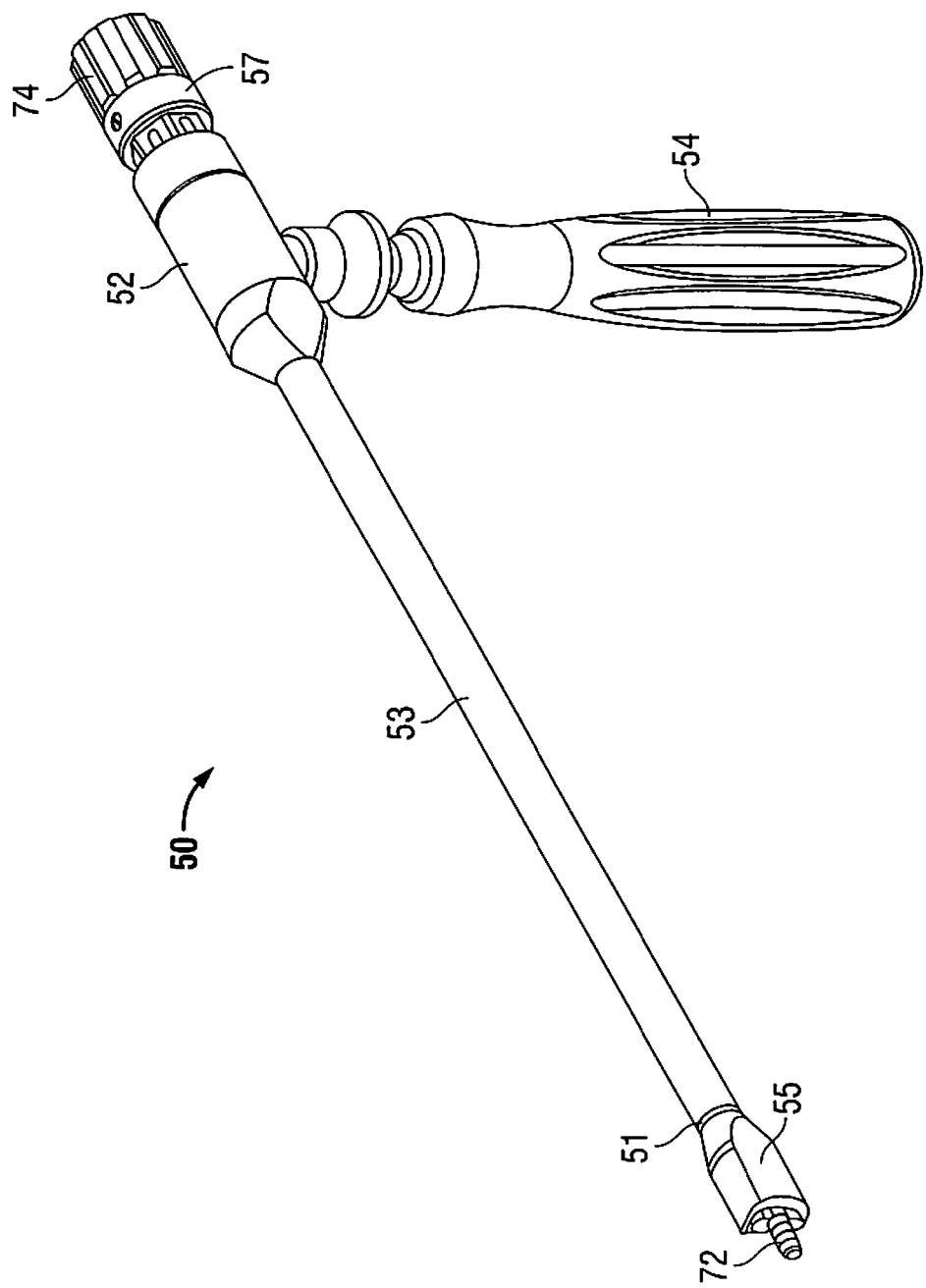
FIG. 14 is a perspective view of an inserter for use with the spinal interbody spacer of FIG. 10-12 or 13A-13B.

With particular reference to FIG. 12, arcuate proximal wall 926 includes a recess 930 defining a threaded aperture 935 for mating with an insertion tool 50 (FIG. 14). Top and bottom surfaces 922, 924 of spacer 900 are substantially parallel to one another. However, it is also envisioned that in another embodiment of a spacer 1900 top and bottom surfaces 1922, 1924 of spacer 1900 may contain lordosis and are not substantially parallel (FIGS. 13A and 13B). Further still, spacer 900 may be tapered laterally defining a generally wedge shaped configuration. In particular, one sidewall may have a height that is different from the height of the opposing sidewall defining the tapered or lordotic configuration. Alternatively, the opposing sidewalls may have the same height, and thus defining a parallel configuration.

Figure 15:
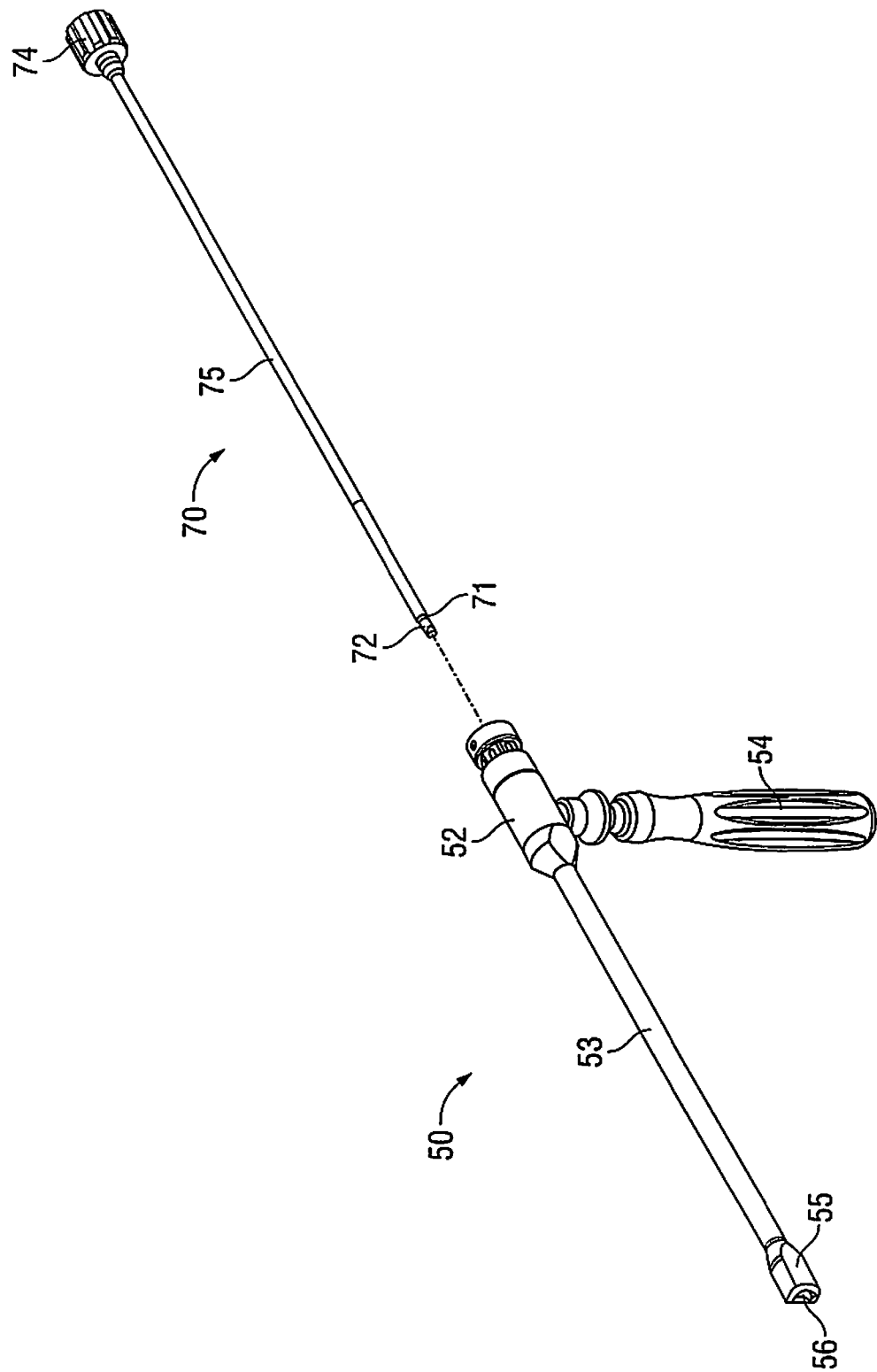
FIG. 15 is an exploded perspective view of the inserter of FIG. 14 with parts separated.

With reference to FIGS. 14 and 15, insertion tool 50 may be utilized to insert spacer 900 between vertebral bodies. Insertion tool 50 includes a housing 52 having a tubular member 53 extending therefrom. A handle 54 extends from housing 52 and is orthogonal to tubular member 53. A coupling 55 is disposed at a distal end 51 of tubular member 53 and is configured and adapted for mating with arcuate proximal wall 926 of spacer 900. A lumen 56 extends from distal end 51 of coupling 55 to a proximal end 57 of housing 52. Inserter rod 70 is repositionable through housing 52 and tubular member 53. Inserter rod 70 has a threaded portion 72 at its distal end 71 that is configured for threadably engaging threaded aperture 935 of spacer 900. A knob 74 is disposed in opposition to threaded portion 72 with a shaft 75 extending therebetween.

Figure 8:
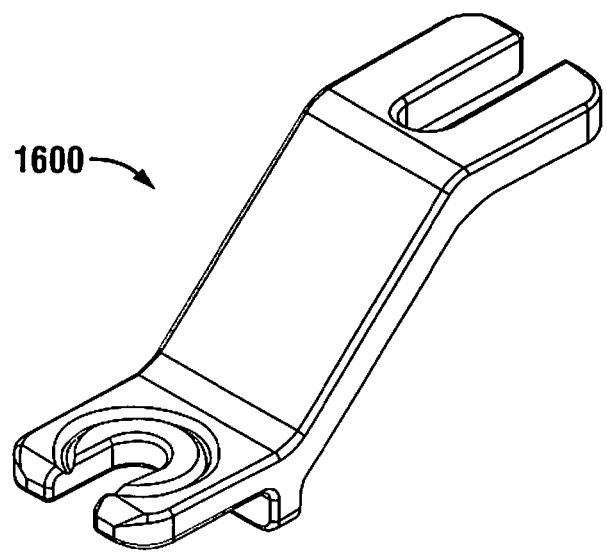
FIG. 8 is a perspective view of an optional table mount for use with the retractor system of FIG. 1.
Figure 9A:
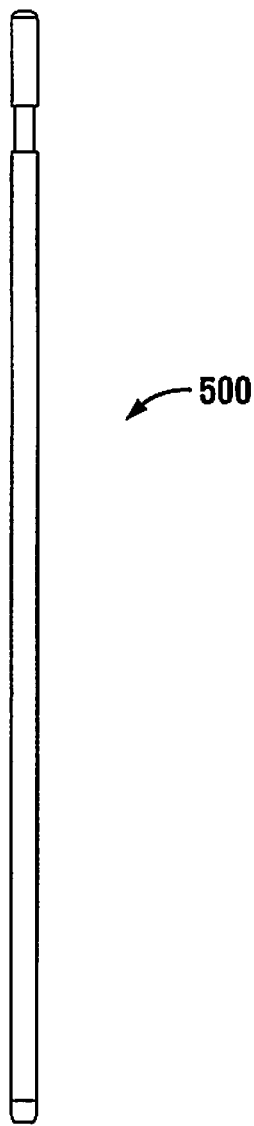
FIG. 9A is a side view of a dissector for use with the retractor system of FIG. 1.
Figure 9B:
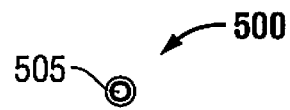
FIG. 9B is a cross-sectional view of the dissector of FIG. 9A.
Figure 9E:
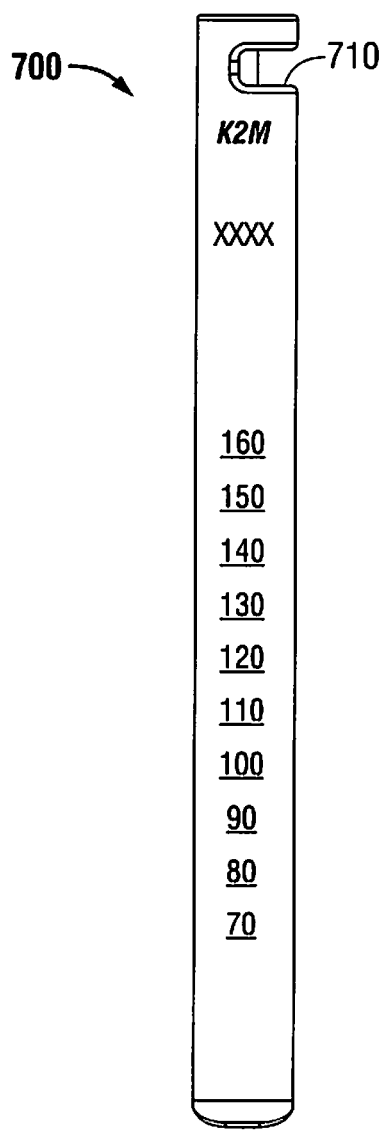
FIG. 9E is a side view of still another dissector for use with the retractor system of FIG. 1.
Figure 9F:
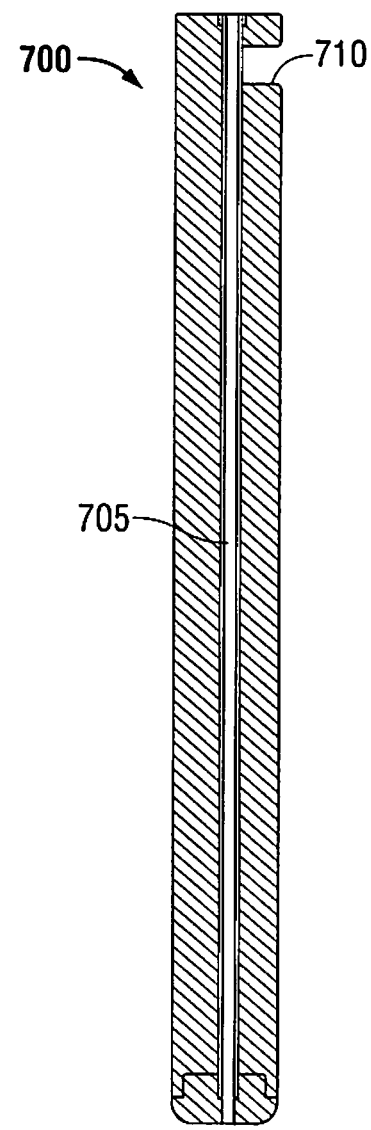
FIG. 9F is a side cross-sectional view of the dissector of FIG. 9E.

It is also envisioned that if additional support for retractor 100 system is necessary, a table mounted surgical arm (not shown) may be attached to the frame with the use of a stabilization arm adapter 1600 (FIG. 8). It is further contemplated that illumination structure such as fiber optics, LED, may be utilized with retractor blade 200 to assist in visualization. Alternatively, a portion of blade portion 208 of retractor blade 200 may be clear plastic and act as light channels themselves.

In use, the clinician positions the patient in a lateral decubitus position on an operating table having a table break such that the patient's iliac crest is directly over the table break. The patient may be secured in position using tape at several locations while avoiding undue pressure points. The clinician uses fluoroscopy or another imaging modality to identify the correct operative level and makes one or more incisions through the patient's skin using conventional instruments. The number and type of incisions made (e.g. transverse or vertical) is related to the procedure to be performed. Subsequently, the subcutaneous tissue layers are taken down exposing the oblique fascia. The muscle fibers are carefully separated as a finger is advanced into the retroperitoneal space. The peritoneum is safely released anteriorly as the retroperitoneal space is further developed. Finger palpation of the psoas muscle or the anterior tip of the transverse process is used to confirm proper location.

Figure 26:
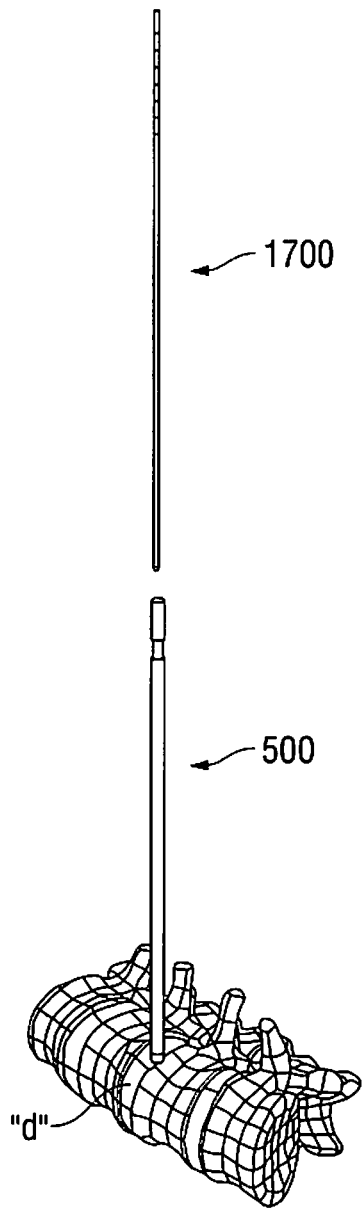
FIGS. 26 and 27 are perspective views of the dissector of FIG. 24 and a guide wire of FIG. 23 illustrating insertion of the guide wire through the dissector.
Figure 27:
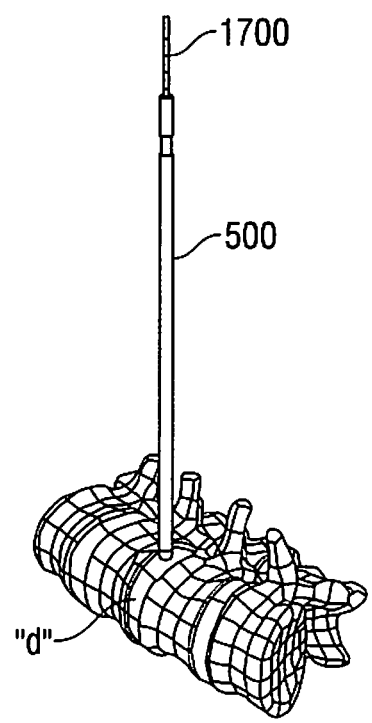
Figure 28:
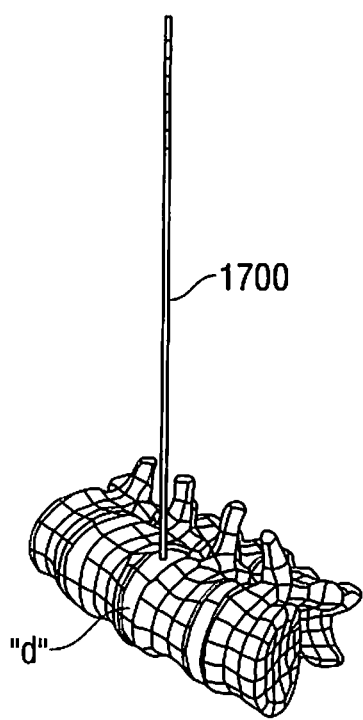
FIG. 28 is a perspective view of the guide wire of FIG. 26 illustrating the guide wire inserted in the disc.
Figure 29:
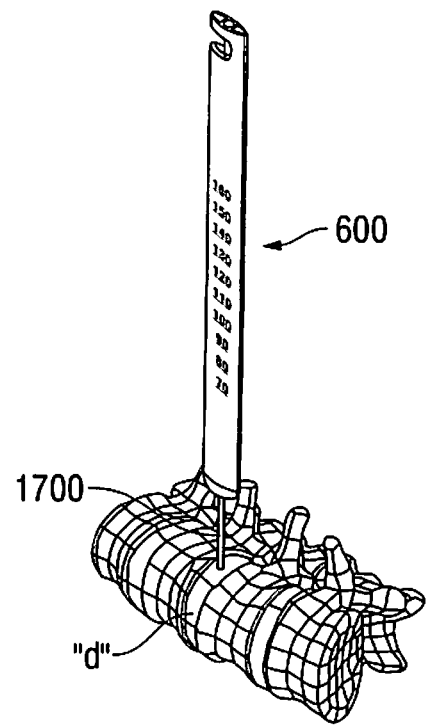
FIGS. 29 and 30 are perspective views of the guide wire of FIG. 28 and the dissector of FIGS. 9C and 9D illustrating insertion of the dissector over the guide wire to enlarge the opening in tissue.
Figure 30:
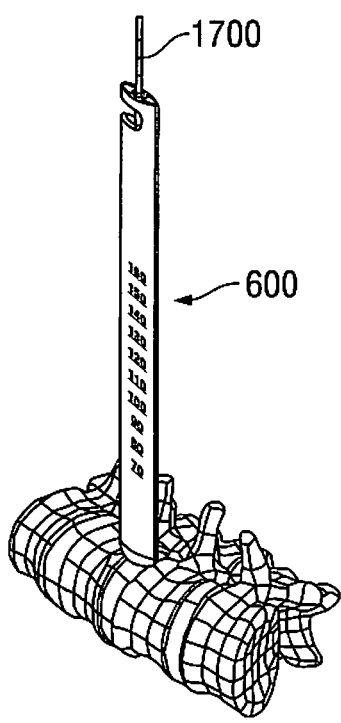
Figure 31:
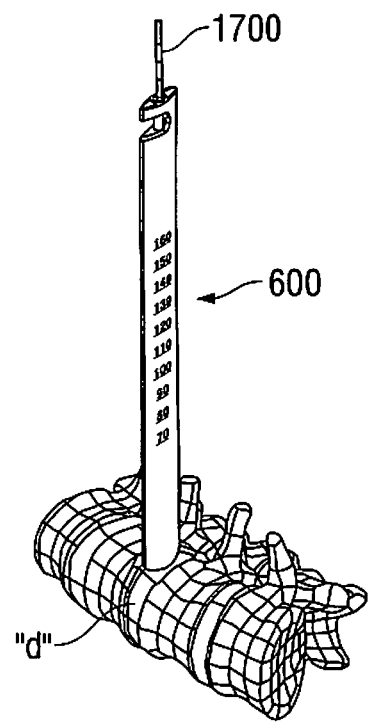
FIG. 31 is a perspective view of the dissector and the guide wire of FIG. 30 illustrating rotation of the dissector to free up soft tissue.

Once verified, dissector 500 (FIG. 9A) is introduced into the prepared path and advanced through the psoas muscle, as shown in FIG. 24. Staying anterior to the lumbar plexus, dissector 500 is docked directly into the middle of disc "d," as shown in FIG. 25. Thereafter, guide wire 1700 (FIG. 23) is inserted through dissector 500 into disc "d,' as shown in FIGS. 26 and 27. Dissector 500 is removed, leaving guide wire 1700 in place, as shown in FIG. 28. One or more larger dissectors 600, 700 may be introduced over guide wire 1700 to enlarge the opening, as shown in FIG. 30. The clinician may use, for example, a slight windshield wiper motion, anterior to posterior, to free up soft tissue. The clinician manipulates dissector 600 along the line of the muscle fibers of the psoas, to thereby minimize trauma, as seen in FIG. 31. Advantageously, dissectors 600,700 are wider in one direction that the other (see FIG. 9E), which facilitates insertion of the dissector between fibers of the psoas muscle with the dissector oriented such that wider profile is aligned with the fibers and the thinner profile is oriented transverse to the psoas muscle fibers. Optionally, the surgeon may connect an electromyography system to one or more of the dissectors to monitor nerve activity during insertion and movement of the dissector.

After an adequate initial path to the spine is prepared in this manner utilizing distractor(s), blade length may be determined by any one of the dissectors 500, 600, 700 in relation to skin level. The clinician may readily determine an appropriate blade length for retractor system 100 by reading the indicia shown on dissector 500, 600, 700. Upon determining the appropriate blade length, the clinician prepares retractor system 100 for use by selecting retractor blades with the desired length and releasably attaching a pair of retractor blades 200 to the first and second support 110, 120 of the retractor system 100.

Figure 33:
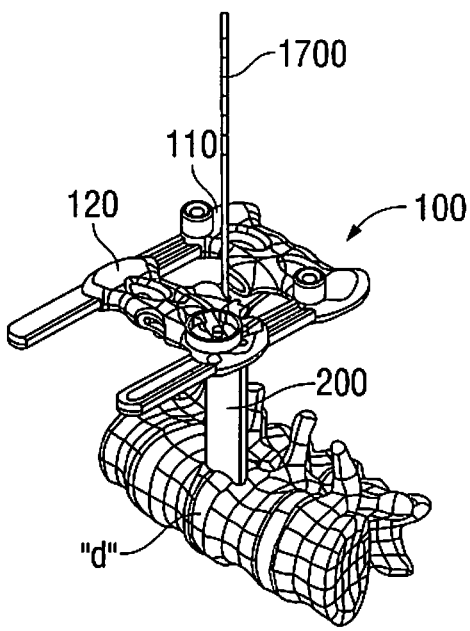
FIG. 33 is a perspective view of the retractor system of FIG. 32A illustrating the retractor system advanced directly to the spine.
Figure 34A:
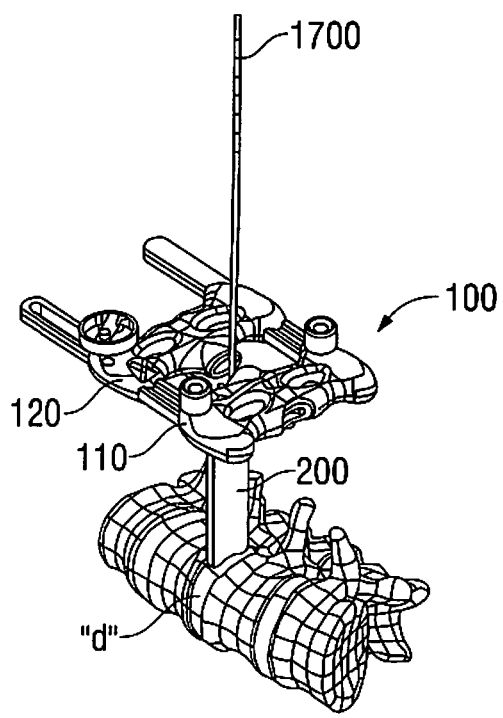
FIG. 34A is a perspective view of the retractor system of FIG. 33 illustrating rotation thereof approximately 90 degrees.
Figure 34B:
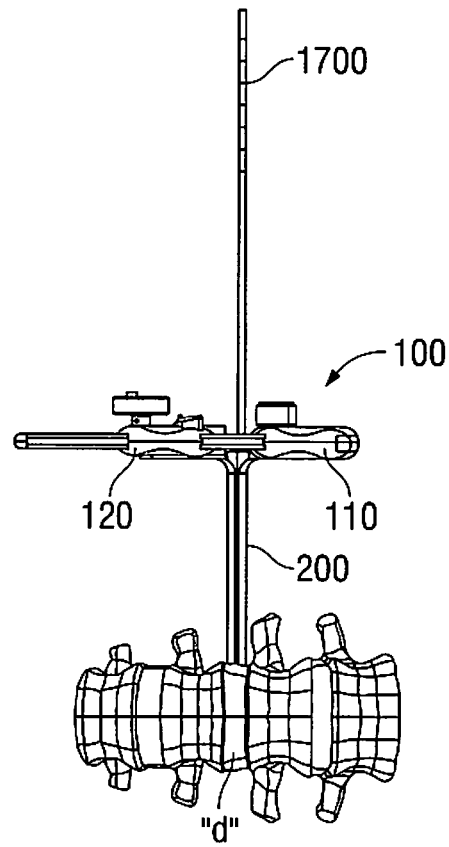
FIG. 34B is a side view of the retractor system of FIG. 34A.

Second support 120 is translated along the arms 130, 132 towards first support 110 such that retractor blades 200 are in close cooperative alignment, as shown in FIG. 32A. The clinician then removes dissector 600, 700 and inserts retractor system 100 with the closed retractor blades 200 into the prepared opening and along the longitudinal axis of the psoas muscle fibers. The retractor may be inserted over guide wire 1700 with guide wire 1700 extending through a lumen defined by longitudinal channel 209. Retractor system 100 is kept in line with the muscle fibers and advanced directly to the spine until the distal tips of the blades are adjacent the spine, as shown in FIG. 33. Advantageously, the low profile of the closed retractor blades permits the blades to be worked between the fibers of the psoas muscle until the distal tips of the blades pass through the psoas muscle and may be positioned adjacent the vertebrae. Retractor system 100 is then turned approximately 90° so that the orientation of retractor blades 200 is in line with the endplates of the vertebrae, as shown in FIGS. 34A and 34B.

Figure 21:
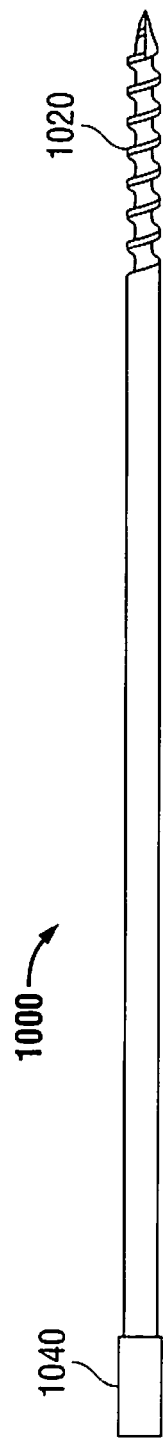
FIG. 21 is a side view of a fixation pin for use with the retractor system of FIG. 1.
Figure 22:
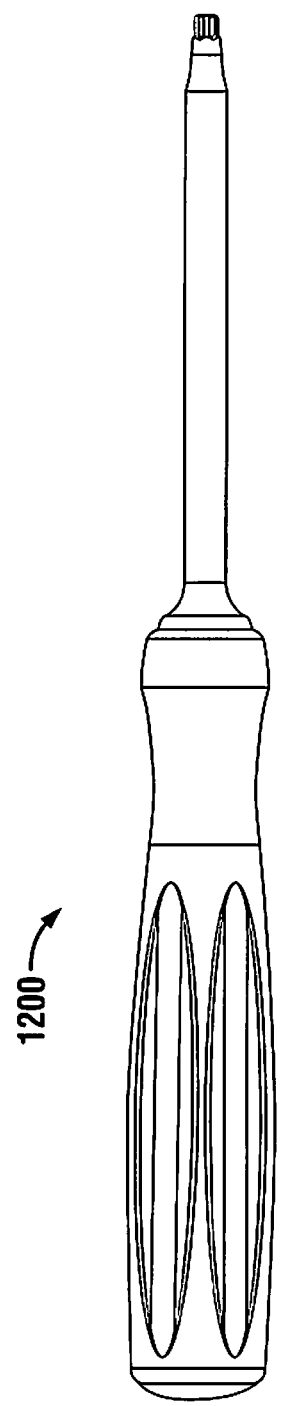
FIG. 22 is a side view of a fixation pin driver for use with the fixation pin of FIG. 21.
Figure 35B:
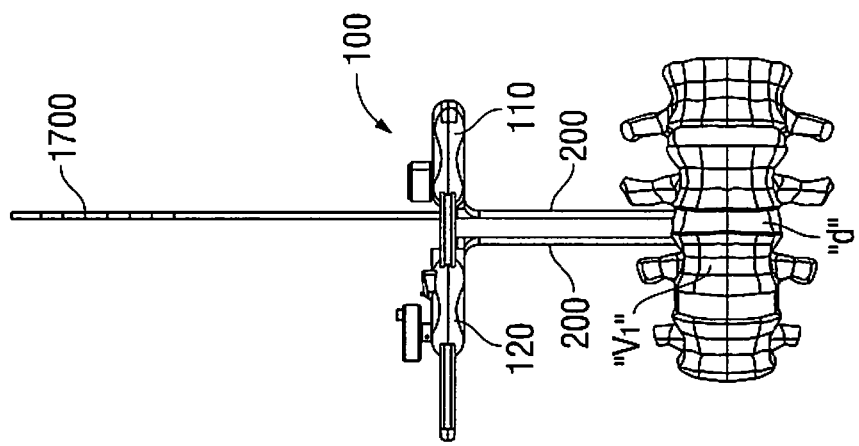
FIG. 35B is a side view of the retractor system of FIG. 35A.
Figure 35A:
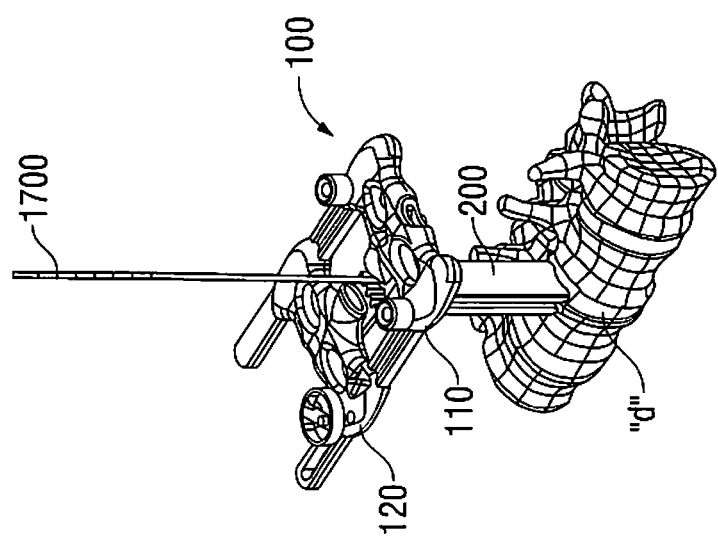
FIG. 35A is a perspective view of the retractor system of FIG. 34A illustrating the retractor system retracted to a partially opened position.
Figure 36B:
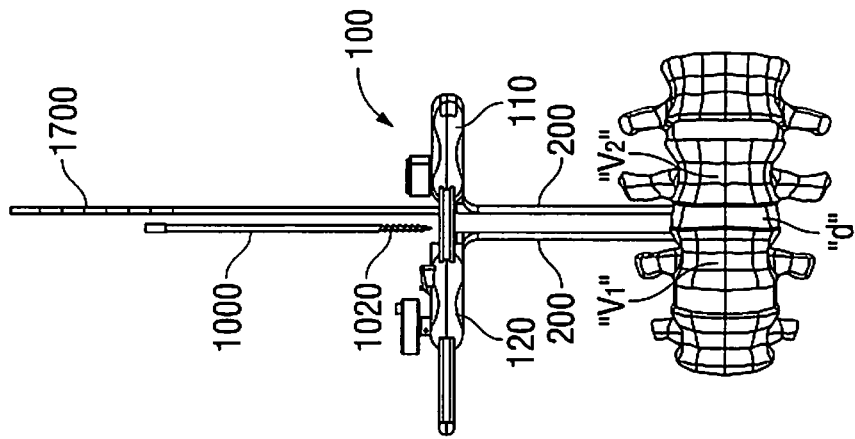
FIG. 36B is a side view of the retractor system of FIG. 36A.
Figure 36A:
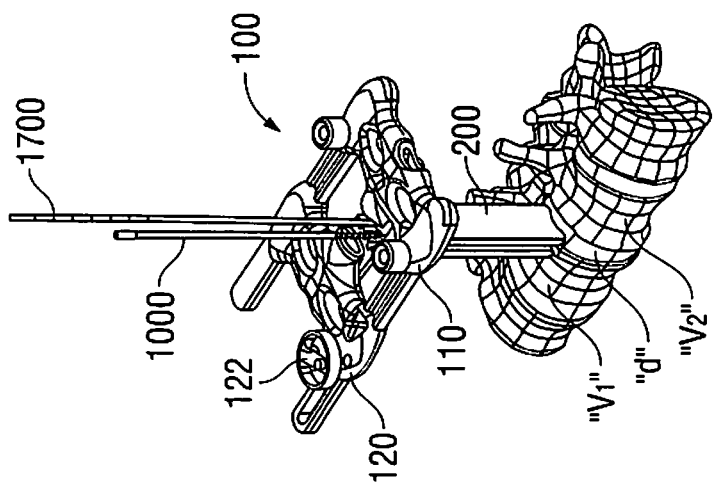
FIG. 36A is a perspective view of the retractor system of FIG. 35A and a fixation pin of FIG. 21 illustrating insertion of the fixation pin into a first vertebra through a longitudinal channel of the retractor blades.
Figure 37:
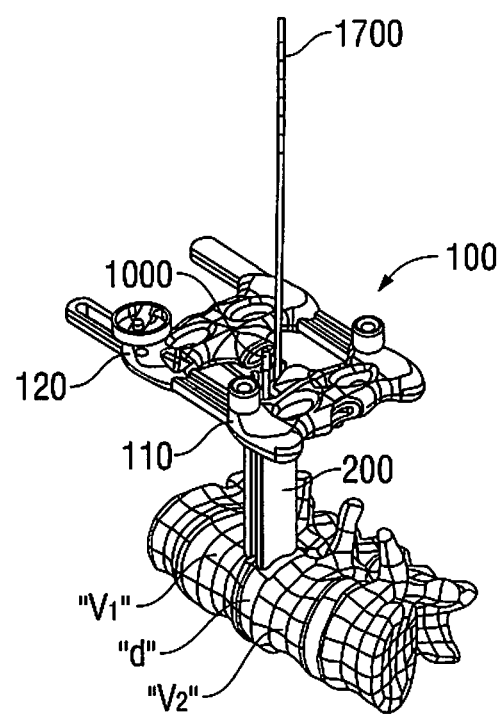
Figure 39A:
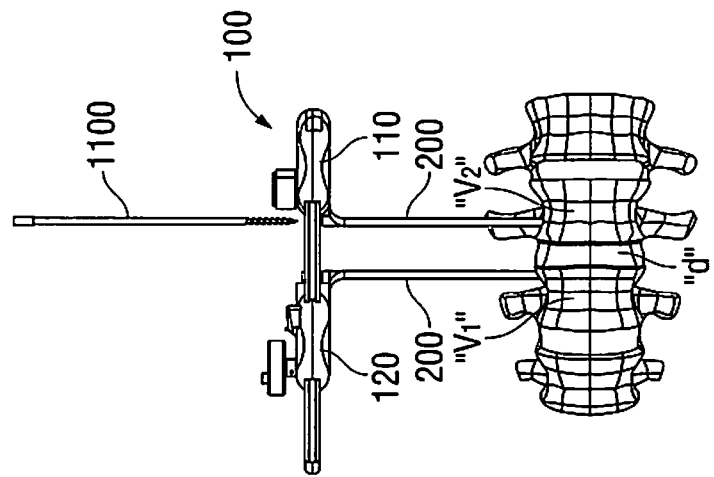
FIG. 39A is a perspective view of the retractor system of FIG. 38A in a more fully open position and the fixation pin of FIG. 21 illustrating insertion of the fixation pin into a second vertebra.
Figure 39B:
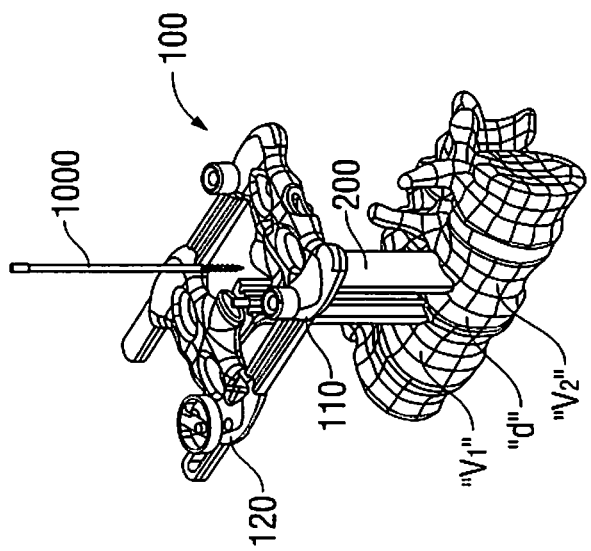
FIG. 39B is a side view of the retractor system of FIG. 39A.

Once retractor system 100 is aligned with the retractor blades 200 substantially transverse to the psoas muscle, retractor system 100 is moved or retracted partially open so that the superior retractor blade is disposed over the adjacent vertebral body, as shown in FIGS. 35A and 35B. Optionally, one or more fixation pins 1000 (FIG. 21) may be introduced through one or more of channels 209 of retractor blade 200 and advanced into vertebra "$V_1$" using a fixation pin driver 1200 (FIG. 22), as shown in FIGS. 36A and 36B. Preferably, fixation pin 1000 has a threaded distal portion 1020 for fixedly engaging bone structures and a head 1040 that is operatively coupled to fixation pin driver 1200 for inserting or removing fixation pin 1000. With the superior blade affixed to the superior vertebra "$V_1$," knob 122 is actuated to move first support 110 away from second support 120, as shown in FIG. 37. However, it is also contemplated that with first support 110 affixed to the superior vertebra "$V_1$," knob 122 may be actuated to move second support 120 from first support 110. A slidable crank arm 123 (FIG. 1) may be extended outward from the knob 122 for additional cranking leverage. As first support 110 moves away from second support 120, as shown in FIGS. 38A and 38B, the ratchet associated with the second arm engages ratchet teeth 136 to prevent first support 110 from returning towards the second support 120 under pressure from the retracted tissue. Retractor system 100 is opened until adequate access and visualization of disc "d" is attained. If additional soft tissue retraction is desired, auxiliary blades 400 for lateral aspect of retractor system 100 may be used. In particular, auxiliary blades 400 are inserted into the incision, drawn back along arms 130, 132 and locked into place by rotating locking wheel 135, 137. The concave distal tips of the blades conform substantially to the curvature of the side of the corresponding vertebra "$V_1$," "$V_2$." This shape advantageously minimizes soft tissue creeping under the blade tip to obstruct a portion of the operative channel. Fixation pins 1000 assist in securing blades 200 to the vertebra to hold the distal blade tips in position against the vertebral bodies "$V_1$," "$V_2$" to assure that retracted tissue does not slip under blades 200 into the operative field as retractor system 100 is leveraged and manipulated during surgery.

An intradiscal shim 1300 (FIG. 16) may also be used to ensure minimal soft tissue creep during instrumentation. Intradiscal shim 1300 is introduced into channel 409 of auxiliary blade 400 and may be advanced directly into the disc space using a shim inserter tool 1400 (FIG. 17). Intradiscal shim 1300 is removed using an extractor tool 1450 (FIG. 18).

Figure 19:
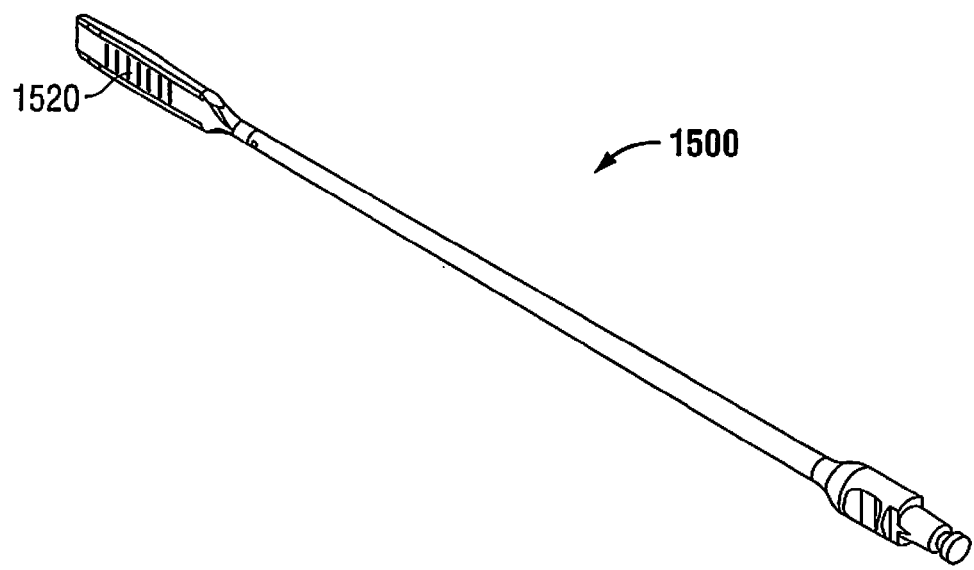
FIG. 19 is a perspective view of a disc spreader for use with the retractor system of FIG. 1.
Figure 20:
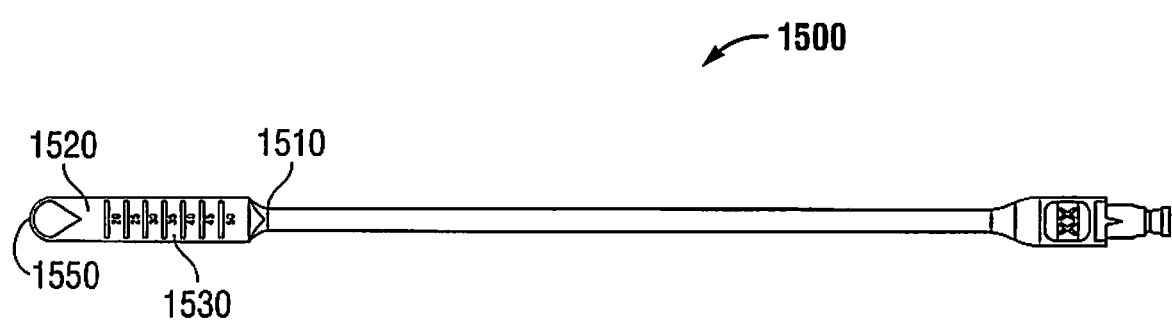
FIG. 20 is a side view of the disc spreader of FIG. 19.

If additional stabilization is desired, an optional table mount arm 1600 (FIG. 8) is attached to retractor system 100 and coupled to an external support (not shown). Once the desired access is achieved, traditional annulotomy and discectomy are performed as well as the release of the contralateral annulus. A selection of disc preparation instruments including a variety of curettes, ronguers, rasps, chisels, and cobbs may also be used. In cases of extremely collapsed discs, a disc spreader 1500 (FIGS. 19 and 20) having a flattened blade portion 1520 at a distal end 1510 thereof may be used to adequately distract the disc space. Blade portion 1520 may also include a plurality of markings 1530 that indicate a distance from a distal end 1550 of blade portion 1520. Distraction is performed until the desired height is achieved. If implant 900 is to be inserted into the intervertebral space, a series of trial implants (not shown) may be used prior to deploying spinal interbody spacer 900. Trial implants may be configured in both lordotic and parallel versions.

After the surgeon determines the appropriate type and size of interbody spacer 900, interbody spacer 900 is inserted using implant insertion tool 50. The inserter rod 70 and handle 54 are coupled together and the selected spinal interbody spacer 900 is threaded on distal end 71 of inserter rod 70 adjacent coupling 55 of distal end 51 of tubular member 53. A mallet and slap hammer (not shown) may also be used to facilitate placement of interbody spacer 900. Once spacer 900 is positioned in the desired location, intradiscal shim 1300 and auxiliary blades 400, if used, and any fixation pins 1000 are removed, ratchet release arm 124 is actuated to permit second support 120 to reapproximate towards first support 110, and retractor system 100 is removed from the incision, which may be closed in a traditional manner.

It is within the scope of the present disclosure that fixation pins 1000 may be used at any point during the procedure or they may not be used at all during the procedure. It will be understood that various modifications may be made to the embodiments of the presently disclosed lateral access system. For example, it is also contemplated that the spacer can be inserted over a rail system such as that shown in U.S. Pat. No. 7,615,079 to Flickinger et al., the contents of which are incorporated by reference herein in their entirety. It is further contemplated that the spacer can be assembled in situ over rails on both sides of the inserter with the tip of the inserter becoming a part of the implant as shown in U.S. Published Application US2009/0228110 to McClintock, the contents of which are incorporated by reference herein in their entirety. In addition, while the systems and methods of the present disclosure have been illustrated in the context of a single level spinal fusion procedure, it is contemplated that the systems and methods may be utilized for multiple level fusions or in a procedure in which an entire vertebra is removed and replaced with an appropriately sized implant. Therefore, the above description should not be construed as limiting, but merely as exemplifications of embodiments. Those skilled in the art will envision other modifications within the scope and spirit of the present disclosure.

What is claimed is:
1. A method of accessing a spine comprising:
   providing a surgical access system including a retractor having:
      first and second supports, at least one of the first or second supports movable relative to the other; and
      first and second retractor blades coupled to the first and second supports, respectively;
   establishing an initial path to the spine;
   positioning the first and second retractor blades in close approximation;

introducing the retractor through tissue along the initial path to the spine in a first orientation such that the first and second retractor blades are aligned with fibers of a psoas muscle;

rotating the retractor to a second orientation substantially transverse to the first orientation; and moving the first and second supports to a spaced apart position such that the first and second retractor blades are spaced apart from one another to retract tissue and create an operative channel to the spine.

2. The method according to claim 1, wherein rotating the retractor to the second orientation includes rotating the retractor until the first and second retractor blades are aligned with endplates of vertebrae.

3. The method according to claim 1, further comprising after rotating the retractor to the second orientation, inserting a fixation pin along the first retractor blade into a vertebral body to fix the first retractor blade relative to the vertebral body.

4. The method according to claim 1, further comprising after rotating the retractor to the second orientation, inserting a second fixation pin along the second retractor blade into a vertebral body to fix the second retractor blade relative to the vertebral body, and after moving the second support away from the first support, inserting a third fixation pin along the second retractor blade into an adjacent vertebral body to fix the second retractor blade relative to the adjacent vertebral body.

5. The method according to claim 1, further comprising removing disc material.

6. The method according to claim 5, further comprising positioning a spinal implant between vertebral bodies after removing the disc material.

7. The method according to claim 1, further comprising distracting a disc utilizing a disc spreader.

8. The method according to claim 1, wherein establishing the initial path to the spine includes forming an incision, digitally probing tissue, and inserting a probe towards the spine.

9. The method according to claim 1, wherein rotating the retractor comprises rotating the retractor until the first and second retractor blades are substantially parallel to endplates of vertebrae.

10. The method according to claim 1, wherein rotating the retractor comprises rotating and orienting the retractor so that a distal end portion of at least one of the first or second retractor blades conforms to a corresponding vertebral body.

11. The method according to claim 10, wherein orienting the retractor comprises moving the distal end portion of the at least one of the first or second retractor blades defining a recess into engagement with a side of the corresponding vertebral body.

12. The method according to claim 1, further comprising positioning the first and second retractor blades in a close cooperative position such that longitudinal grooves of the first and second retractor blades define a lumen.

13. The method according to claim 1, further comprising mounting an auxiliary blade transversely to one of the first or second retractor blades.

14. The method according to claim 13, further comprises further comprising introducing an intradiscal shim along a groove of the auxiliary blade and into a disc space.

15. The method according to claim 1, wherein establishing the initial path to the spine includes forming an incision and inserting at least one dissector through the incision towards the spine.

16. The method according to claim 15, further comprising utilizing depth indicia on the at least one dissector to determine a blade length of one of the first or second retractor blades.

17. The method according to claim 1, further comprising performing surgery through the operative channel.

18. A method of accessing a spine comprising:
providing a surgical access system including a retractor having:
first and second supports, at least one of the first or second supports movable relative to the other between close and spaced apart positions; and
first and second retractor blades coupled to the first and second supports, respectively, a distal end portion of at least one of the first or second retractor blades defining a recess including an arcuate portion configured to engage and conform to a shape of a side of a vertebral body;
establishing an initial path to the spine;
introducing the retractor through tissue along the initial path to the spine in a first orientation;
rotating and orienting the retractor so that the recess of the distal end portion of the at least one of the first or second retractor blades is in engagement with the vertebral body; and
moving the first and second supports to a spaced apart position such that the first and second retractor blades are spaced apart from one another to retract tissue and create an operative channel to the spine.

19. The method according to claim 18, further comprising rotating the retractor to a second orientation transverse to the first orientation.

20. The method according to claim 18, further comprising performing surgery through the operative channel.

21. The method according to claim 18, further comprising inserting a fixation pin along the first retractor blade into a vertebral body to fix the first retractor blade relative to the vertebral body.

22. The method according to claim 21, further comprising inserting a second fixation pin along the second retractor blade into an adjacent vertebral body to fix the second refractor blade relative to the adjacent vertebral body after moving the second support away from the first support.

23. The method according to claim 22, further comprising positioning a spinal implant between the vertebral bodies after removing disc material.

24. The method according to claim 18, wherein introducing the retractor through tissue in the first orientation includes inserting the retractor with the first and second retractor blades substantially aligned with fibers of a psoas muscle.

25. The method according to claim 20, wherein performing surgery includes distracting a disc utilizing a disc spreader.

26. The method according to claim 18, wherein establishing the initial path to the spine includes forming an incision, digitally probing tissue, and inserting a probe towards the spine.

27. The method according to claim 18, wherein rotating the retractor comprises rotating the retractor until the first and second retractor blades are substantially parallel to endplates of vertebrae.

28. The method according to claim 18, further comprising placing the first and second retractor blades in a close cooperative arrangement such that longitudinal grooves of the first and second retractor blades define a lumen.

29. The method according to claim 18, further comprising mounting an auxiliary blade transversely to one of the first or second retractor blades.

30. The method according to claim 29, further comprising introducing an intradiscal shim along a groove of the auxiliary blade and into a disc space.

31. The method according to claim 18, wherein establishing the initial path to the spine includes forming an incision and inserting at least one dissector through the incision towards the spine.

32. The method according to claim 31, further comprising utilizing depth indicia on the at least one dissector to determine a blade length of one of the first or second retractor blades.

33. A method of accessing a spine comprising:
providing a surgical access system including a retractor having:
a first support;
a second support movable between a first position adjacent the first support and a second position spaced apart from the first support; and
first and second retractor blades releasably coupled to the first and second supports, respectively, the first and second retractor blades assuming a position in close approximation when the first and second supports are in the first position, and a second, open position when the first and second supports assume the second position spaced apart from each other;
establishing an initial path to the spine;
introducing the retractor through tissue along the initial path to the spine in a first orientation, the retractor being inserted with the first and second supports in the first position and with the first and second retractor blades in close approximation;
rotating the retractor to a second orientation such that the first and second retractor blades are substantially parallel to endplates of vertebrae;
moving the first and second supports to the second, spaced apart position such that the first and second retractor blades are spaced apart from one another to retract tissue and create an operative channel to the spine; and
performing surgery through the operative channel.

34. The method according to claim 33, further comprising inserting a fixation pin along the first retractor blade into a vertebral body to fix the first retractor blade relative to the vertebral body after rotating the retractor to the second orientation.

35. The method according to claim 34, further comprising inserting a second fixation pin along the second retractor blade into an adjacent vertebral body to fix the second retractor blade relative to the adjacent vertebral body after rotating the retractor to the second orientation.

36. The method according to claim 34, further comprising inserting a third fixation pin along the second retractor blade into an adjacent vertebral body to fix the second retractor blade relative to the adjacent vertebral body after moving the second support away from the first support.

37. The method according to claim 35, further comprising positioning a spinal implant between the vertebral bodies after removing disc material.

38. The method according to claim 33, wherein introducing the retractor through tissue in the first orientation comprises inserting the retractor with the first and second retractor blades substantially aligned with fibers of a psoas muscle.

39. The method according to claim 33, further comprising distracting a disc utilizing a disc spreader.

40. The method according to claim 33, wherein establishing the initial path to the spine includes forming an incision, digitally probing tissue, and inserting a probe towards the spine.

41. The method according to claim 33, wherein rotating the retractor comprises rotating and orienting the retractor so that a distal end portion of at least one of the first or second retractor blades conforms to a corresponding vertebral body.

42. The method according to claim 41, wherein orienting the retractor comprises moving the distal end portion of the at least one of the first or second retractor blades defining a recess into engagement with the corresponding vertebral body.

43. The method according to claim 33, further comprising positioning the first and second retractor blades in a close cooperative position the arrangement such that longitudinal grooves of the first and second retractor blades define a lumen.

44. The method according to claim 43, further comprising inserting at least one fixation pin through the lumen into the corresponding vertebral body to fix the first or second retractor blades relative to the corresponding vertebral body after rotating the retractor to the second orientation.

45. A method of accessing a spine comprising:
providing a surgical access system including a retractor having:
first and second supports, at least one of the first or second supports movable relative to the other between close and spaced apart positions; and
first and second retractor blades coupled to the first and second supports, respectively, a distal end portion of at least one of the first or second retractor blades defining a recess configured to engage and conform to a shape of a side of a vertebral body;
establishing an initial path to the spine;
introducing the retractor through tissue along the initial path to the spine in a first orientation;
rotating and orienting the retractor so that the recess of the distal end portion of the at least one of the first or second retractor blades is in engagement with the vertebral body;
moving the first and second supports to the spaced apart position such that the first and second retractor blades are spaced apart from one another to retract tissue and create an operative channel to the spine; and
inserting a fixation pin along the first retractor blade into the vertebral body to fix the first retractor blade relative to the vertebral body.

46. The method according to claim 45, further comprising rotating the retractor to a second orientation transverse to the first orientation.

47. The method according to claim 45, further comprising performing surgery through the operative channel.

48. method according to claim 45, further comprising inserting a second fixation pin along the second retractor blade into an adjacent vertebral body to fix the second retractor blade relative to the adjacent vertebral body after moving the second support away from the first support.

49. The method according to claim 45, further comprising placing the first and second retractor blades in a close cooperative arrangement such that longitudinal grooves of the first and second retractor blades define a lumen.

50. The method according to claim 48, further comprising positioning a spinal implant between the vertebral bodies after removing disc material.

51. The method according to claim 45, wherein introducing the retractor through tissue in the first orientation includes inserting the retractor with the first and second retractor blades substantially aligned with fibers of a psoas muscle.

52. The method according to claim 45, wherein establishing the initial path to the spine includes forming an incision, digitally probing tissue, and inserting a probe towards the spine.

53. The method according to claim 45, wherein rotating the retractor comprises rotating the retractor until the first and second retractor blades are substantially parallel to endplates of vertebrae.

54. The method according to claim 45, further comprising mounting an auxiliary blade transversely to one of the first or second retractor blades.

55. The method according to claim 54, further comprising introducing an intradiscal shim along a groove of the auxiliary blade and into a disc space.

56. The method according to claim 45, wherein establishing the initial path to the spine includes forming an incision and inserting at least one dissector through the incision to the spine.

\* \* \* \* \*